United States Patent [19]

Walsh

[11] Patent Number: 5,057,524
[45] Date of Patent: Oct. 15, 1991

[54] 4-[DIARYL)HYDROXYMETHYL]-1-PIPERIDINEALKYLCARBOXYLIC ACIDS, SALTS AND ESTERS USEFUL IN THE TREATMENT OF ALLERGIC DISORDERS

[75] Inventor: David A. Walsh, Richmond, Va.

[73] Assignee: A. H. Robins Company Incorporated, Richmond, Va.

[21] Appl. No.: 476,803

[22] Filed: Feb. 8, 1990

[51] Int. Cl.$^5$ .................. A61K 31/445; C07D 211/32
[52] U.S. Cl. ..................................... 514/317; 514/318; 514/331; 546/193; 546/194; 546/233; 546/234; 546/238; 546/239
[58] Field of Search ............... 546/193, 194, 233, 234, 546/239, 238; 514/318, 317, 331

[56] References Cited

U.S. PATENT DOCUMENTS

| | | | |
|---|---|---|---|
| 3,045,023 | 7/1962 | Rorig | 546/235 |
| 3,806,526 | 4/1974 | Carr et al. | 546/190 |
| 3,922,276 | 11/1975 | Duncan et al. | 546/192 X |
| 3,956,296 | 5/1976 | Duncan et al. | 546/189 X |
| 4,032,642 | 6/1977 | Duncan et al. | 514/237.2 |
| 4,525,358 | 6/1985 | Baltes et al. | 514/255 |
| 4,810,713 | 3/1989 | Yanni et al. | 514/317 |

*Primary Examiner*—Mary C. Lee
*Assistant Examiner*—Jacqueline Haley
*Attorney, Agent, or Firm*—Richard K. Jackson

[57] ABSTRACT

Novel compounds useful in the treatment of allergic disorders and having the formula:

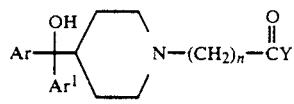

where Ar and Ar$^1$ are pyridinyl, phenyl, or substituted phenyl and where Y is —OH, —O$^\ominus$M$^\oplus$m, —O—loweralkyl, —O—Aryl, or NR$^1$R$^2$(R$^1$, R$^2$=H, loweralkyl, aryl) are herein disclosed.

15 Claims, No Drawings

4-[DIARYL)HYDROXYMETHYL]-1-PIPERIDINEALKYLCARBOXYLIC ACIDS, SALTS AND ESTERS USEFUL IN THE TREATMENT OF ALLERGIC DISORDERS

BACKGROUND OF THE INVENTION

1. Field of Invention

This invention relates to novel α,α-diaryl-4-piperidinemethanols having an alkylcarboxylic acid, salt, ester or amide group attached to the piperidine nitrogen and their use in treating allergic disorders in a living animal body. This invention thus contemplates the use of these novel compounds in treating allergic disorders, particularly Type I allergic responses (Gell and Coombs classification) which includes but is not limited to asthma, rhinitis, atopic dermatitis, chronic hives, allergic conjunctivitis and the like.

2. Information Disclosure Statement

4-[bis(4-fluorophenyl)methyl]-1-piperidinepropanamide was disclosed in a commonly owned U.S. Pat. No. 3,956,296 as having antiinflammatory, sedative, and tranquilizing properties. Compounds of following formula

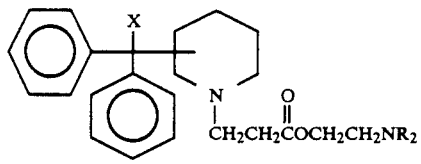

where X is hydrogen or hydroxy and R is $C_1$–$C_9$ alkyl are described in U.S. Pat. No. 3,045,023 as being useful antibacterial and antifungal agents which also manifest eurythmic and antiinflammatory properties and appear to depress the central nervous system. The compounds of this invention differ in that they are not esters of aminoalkanols and further differ in that the additional basic nitrogen is absent.

A similar compound incorporating the piperazine ring as shown below is described in the

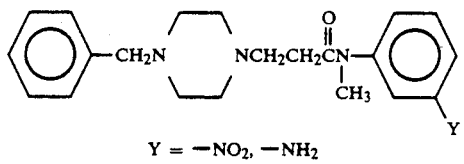

$Y = -NO_2, -NH_2$

European patent application EPO 207,901 as having antianaphylactic and antibronchospastic activities. Heterocyclic alkoxyacetic acid derivatives of the formula below where X is —OH or —NH$_2$ or NR$^1$R$^2$

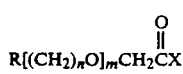

and R is 4-(diarylmethyl)piperazine or 4-diarylmethylenepiperidine are described in U.S. Pat. No. 4,525,358 and European Patent Application 048,705 as having antiallergy and antihistamine properties. One of these compounds, 2-[2-[2-[4-(diphenylmethylene)-1-piperidinyl]ethoxy]ethoxy]acetic acid is the subject of a report in Eur. J. Clin. Pharmacol. 28(5), 517–521 (1985).

SUMMARY OF THE INVENTION

The novel compounds which are useful in the antiallergy method of this invention have the general formula:

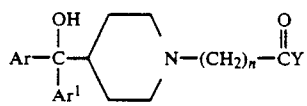

Formula I wherein Ar and Ar$^1$, same or different, are

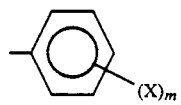

or pyridyl; X is selected from H, —CF$_3$, halogen, loweralkyl, loweralkoxy, or hydroxy and m is 1–3;

n is 1–12;

Y is —OH, —O$^\ominus$M$^\oplus$, O-loweralkyl, —O-aryl, or NR$^1$R$^2$ where R$^1$ and R$^2$, same or different, are H, loweralkyl, or aryl;

M$^\oplus$ is a pharmaceutically acceptable metal ion; and the pharmaceutically acceptable salts thereof, including acid addition salts, quaternary salts, hydrates and solvates thereof.

In the further definition of symbols in the formulas hereof and where they appear elsewhere throughout this specification and claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec-butyl, tert-butyl, amyl, isoamyl, hexyl, heptyl, and octyl radicals and the like. The term "loweralkoxy" has the formula —O-loweralkyl.

The term "halo" or "halogen" when referred to herein includes fluorine, chlorine, bromine and iodine unless otherwise stated.

Aryl is phenyl or phenyl substituted by non-reactive or non-interfering radicals such as halo, loweralkyl, loweralkoxy, and the like.

"Pharmaceutically acceptable salts" include acid addition salts, solvates and quaternary salts of the compounds of Formula I which are physiologically compatible in warm-blooded animals. The acid addition salts may be formed by either strong or weak acids. Representative of strong acids are hydrochloric, hydrobromic, sulfuric, and phosphoric acids. Representative of weak acids are fumaric, maleic, mandelic, tartaric, citric, oxalic, succinic, hexamic, and the like. Suitable quarternary salts include the loweralkyl halides and loweralkyl sulfates.

The primary screening method used to detect antiallergy properties of the compounds of Formula I is a modification of the procedure of R. R. Martel and J. Klicius, Intern. Arch. Allergy Appl. Immunology, Vol. 54, pp 205–209 (1977) which measures the effect of oral administration of the compound on the volume of a rat paw which was previously injected with anti-egg albumin serum and is described in detail under Pharmacology Methods hereinbelow.

The above test is useful in determining the ability of a compound to inhibit Type I allergic responses in a living animal and their usefulness in treating allergic phenomena which includes asthma, rhinitis, atopic dermatitis, chronic hives, allergic conjunctiviti and the like.

The Gell and Coombs Classification of Immune Responses referred to hereinabove is well known in the art and is described in Essential Immunology, 3rd Ed. (1977) (Blackwell Scientific Publications) printed by William Clowes & Sons, Limited, London, Beccles and Colchester.

It is, therefore, an object of this invention to provide novel compounds of Formula I which are useful in treating allergic disorders in warm-blooded animals, including humans. Another object of this invention is to provide a method of treating allergic disorders with novel compounds of this invention. It is another object of this invention to provide a pharmaceutical composition providing a suitable dosage form of compounds of this invention useful in treating allergic disorders. Additional objects will become apparent to one skilled in art and still other objects will become apparent hereinafter.

DETAILED DESCRIPTION OF THE INVENTION

Antiallergy compounds of Formula I above useful in the method of treating allergy of this invention may be prepared by methods described in our commonly owned U.S. Pat. Nos. 3,922,276 and 4,032,642 and 4,810,713 which are hereby incorporated by reference.

The general method used in the detailed examples hereinbelow is outlined by equation in Chart I. This reaction can be carried out in alcoholic solvents, preferably refluxing butanol or in dimethylformamide, dimethoxyethane in the presence of an acid receptor as, for example, an alkali-metal carbonate, and preferably using potassium iodide catalyst. The reaction time may vary from a few hours to 24 hr, depending on reactivity of the haloalkylcarboxylic acid or derivative and temperature. Temperature can vary from about 80° C. to 125° C. Products are isolated, usually by partitioning in a solvent such as methylene chloride, chloroform or benzene and the like and a weak basic aqueous solution and washing, drying and concentrating the organic layer to give the free base which may then be converted, if desired, to an acid addition salt in a conventional manner.

CHART I

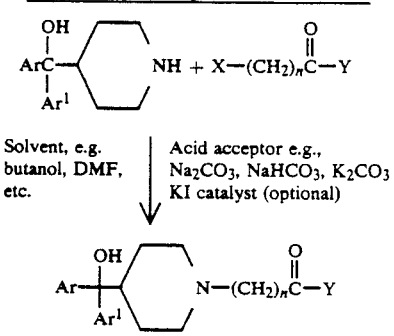

When Y is O-loweralkyl and the carboxylic acid is desired, hydrolysis is accomplished using aqueous sodium bicarbonate solution and ethanol.

To prepare an acid addition salt, the free base is reacted with the calculated amount of organic or inorganic acid in aqueous miscible solvent such as ethanol or 2-propanol, with isolation by concentration and/or cooling, or the base is reacted with an excess of the acid in an aqueous immiscible solvent such as diethyl ether or isopropyl ether, with the desired salt separating directly. Exemplary of such organic salts are those formed with oxalic, maleic, fumaric, benzoic, ascorbic, pamoic, succinic, methanesulfonic, acetic, propionic, tartaric, citric, lactic, malic, citraconic, itaconic, hexamic, p-aminobenzoic, glutamic and stearic acid and the like. Exemplary of such inorganic salts are those formed with hydrochloric, hydrobromic, sulfuric, sulfamic, phosphoric and nitric acids.

If desired, the free base may be regenerated by partitioning the acid addition salt between an organic solvent such as methylene chloride and a weakly basic aqueous solution of, for example, sodium bicarbonate and separating the methylene chloride layer and evaporating it.

The 4-(diarylhydroxymethyl)piperidines used in the synthesis of compounds of Formula I are prepared in several ways as illustrated by the following sets of equations. See also U.S. Pat. Nos. 3,922,276 and 3,956,296 and 4,810,713.

1.

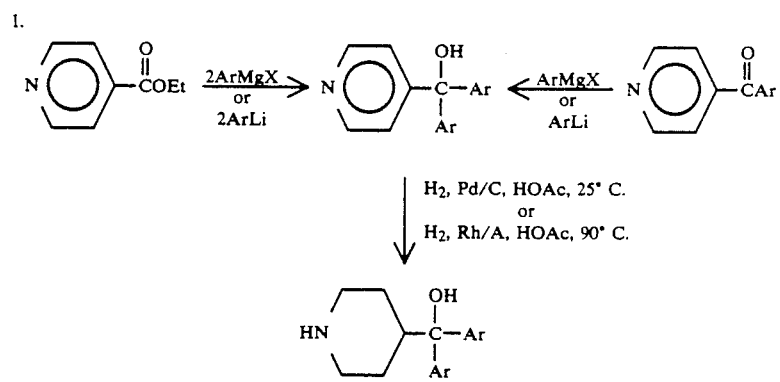

2.

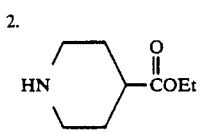

(P = removeable protecting group)

Removal of the protecting group is accomplished using catalytic hydrogenation when P is benzyl, basic hydrolysis when P is acetyl, and reduction with lithium aluminum hydride when P is diethylcarbamoyl.

3.

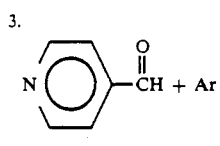

4. When the Ar groups are to be different, the intermediates are prepared from the protected 4-benzoylpiperidines.

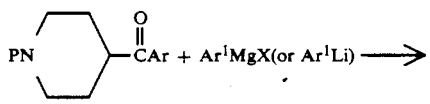

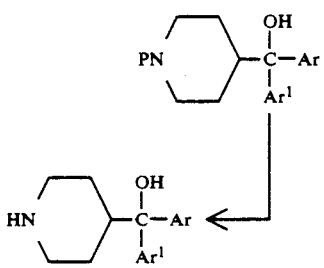

The foregoing methods of preparation of compounds of Formula I are broadly described and the reaction may not be applicable as described to each compound included within the scope of this invention. Where this occurs will be easily recognized by those skilled in the art of organic synthesis and such reactions can be carried out by modifications known to those skilled in the art. Exact conditions may vary with substrates, solvents, reagents, temperature and the like.

Without further elaboration it is believed that one skilled in the art will be able to carry out this invention without undue experimentation. The following preparations and examples are therefore to be construed as illustrative and not limiting to this disclosure in any way. The various reagents used in the following preparations and examples are either commercially available or readily synthesized by literature procedures.

PREPARATION 1

4-Chloro-N-methylbutanamide

A solution of 60.0 g (1.93 mol) of gaseous methylamine in 250 ml of cold methylene chloride ($CH_2Cl_2$) was added dropwise to a solution of 100.0 g (0.71 mole) of 4-chlorobutyryl chloride in 200 ml of $CH_2Cl_2$. The reaction mixture was stirred mechanically and the temperature maintained between 5° and 15° C. throughout the addition. After the final addition, the solution was filtered to remove solid precipitates, and the filtrate was concentrated under reduced pressure. The residue was partitioned between water and $CH_2Cl_2$. The $CH_2Cl_2$ layer was repeatedly washed with water and brine, dried ($MgSO_4$) and concentrated under reduced pressure to yield 44.0 g (46%) of a yellow, amorphous solid. An analytical sample was prepared by recrystallizing the solid from ethyl ether-petroleum ether (30°–60° C.) to give a white solid, mp 33°–34° C.

Analysis: Calculated for $C_5H_{10}ClNO$: C, 44.29; H, 7.43; N, 10.33. Found: C, 43.89; H, 7.54; N, 10.14.

PREPARATION 2

3-Chloro-N-phenylpropanamide

A solution of 5.6 g (0.06 mole) of aniline in 50 ml of tetrahydrofuran was added dropwise to a solution of 5.0 g (0.04 mole) of 3-chloropropionyl chloride in 50 ml of tetrahydrofuran. The reaction mixture was mechanically stirred and the temperature maintained between 5° and 15° C. throughout the addition. After the final addition, the solution was filtered to remove solid precipitates, and the filtrate was concentrated under reduced pressure to give a white solid. The solid was recrystallized from benzene and petroleum ether (30°–60° C.) to yield 5.1 g (69%) of white solid, mp 114°–115° C.

Analysis: Calculated for $C_9H_{10}ClNO$: C, 58.87; H, 5.49; N, 7.53. Found: C, 59.03; H, 5.48; N, 7.69.

PREPARATION 3

3-Chloro-N-methylpropanamide

A solution of 25.0 g (0.805 mole) of gaseous monomethylamine in 150 ml of cold tetrahydrofuran was added dropwise to a solution of 50.0 g (0.394 mole) of 3-chloropropionyl chloride in 100 ml of tetrahydrofuran. The reaction mixture was stirred mechanically, and the temperature maintained between 5° and 15° C. throughout the addition. After the final addition, the solution was filtered to remove a solid precipitate, and the filtrate was concentrated under reduced pressure to yield 44.1 g (92%) of white solid. An analytical sample, mp 52°–55° C., was prepared from ethyl acetate.

Analysis: Calculated for $C_4H_8ClNO$: C, 39.52; H, 6.62; N, 11.52. Found: C, 39.47; H, 6.72; N, 11.43.

PREPARATION 4

5-Chloro-N,N-dimethylpentanamide

A solution of 20.0 g (0.44 mole) of dimethylamine in 100 ml of cold tetrahydrofuran (THF) was added dropwise to a solution of 20.0 g (0.13 mole) of 5-chlorovaleryl chloride in 100 ml of THF. The reaction mixture was stirred mechanically and the temperature maintained between 5° and 15° C. throughout the addition.

After the final addition, the solution was filtered to remove solid precipitates, and the filtrate was concentrated under reduced pressure to yield 18.0 g (85%) of yellow oil. An analytical sample was prepared by filtering this oil through a small bed of silica gel and eluting with ethyl acetate-hexane (1:1). The fractions containing the desired product were combined and concentrated under reduced pressure to give the title compound as a light-yellow oil.

Analysis: Calculated for $C_7H_{14}ClNO$: C, 51.38; H, 8.62; N, 8.56. Found: C, 51.19; H, 8.85; N, 8.28.

PREPARATION 5

3-Chloro-N,N-diphenylpropanamide

To a solution of 40.6 g (0.240 mole) of diphenylamine in 150 ml of tetrahydrofuran (THF) was added dropwise a solution of 20.0 g (0.160 mole) of 3-chloropropionyl chloride in 100 ml of THF. The reaction mixture was stirred mechanically and the temperature maintained between 5° and 15° C. throughout the addition. After the final addition, the solution was filtered to remove solid precipitates, and the filtrate was concentrated under reduced pressure. The residue was partitioned between methylene chloride and water (200 ml each). The methylene chloride layer was washed with water and brine, dried ($MgSO_4$) and concentrated under reduced pressure to give an amorphous solid. The solid was recrystallized from THF to yield 20.0 g (48%) of the title compound as a white, crystalline solid, mp 93°-94° C.

Analysis: Calculated for $C_{15}H_{14}ClNO$: C, 69.37; H, 5.43; N, 5.39. Found: C, 69.31; H, 5.36; N, 5.37.

PREPARATION 6

3-Chloro-N,N-dimethylpropanamide

A solution of 50.0 g (1.110 mole) of dimethylamine in 200 ml cold tetrahydrofuran was added dropwise to a solution of 31.0 g (0.244 mole) of 3-chloropropionyl chloride in 100 ml of tetrahydrofuran. The reaction mixture was stirred mechanically, and the temperature maintained between 5° and 15° C. throughout the addition. After the final addition, the solution was filtered to remove a solid precipitate and the filtrate was concentrated under reduced pressure to give a light-yellow oil. The oil was purified by column chromatography using 150 g of silica gel on a 60 cm×3.5 cm column, eluted with ethyl acetate-hexane (1:1). The fractions containing the desired product were combined and concentrated under pressure to yield 31.2 g (94%) of colorless liquid.

Analysis: Calculated for $C_5H_{10}ClNO$: C, 44.29; H, 7.43; N, 10.33. Found: C, 44.11; H, 7.60; N, 10.11.

PREPARATION 7

3-Chloro-N-methyl-N-phenylpropanamide

A solution of 107.2 g (1.00 mole) of N-methylaniline in 150 ml of tetrahydrofuran was added dropwise to a solution of 90.4 g (0.71 mole) of 3-chloropropionyl chloride in 250 ml of tetrahydrofuran. The reaction temperature was maintained between 5° and 15° C. throughout the addition. After the final addition, the solution was filtered to remove a solid precipitate, and the filtrate was concentrated under reduced pressure to yield 130.0 g (91%) of a dark oil. An analytical sample was prepared by filtering the oil through a small bed of silica gel and eluting with ethyl acetate-hexane (1:5). The fractions containing the desired product were combined and concentrated under reduced pressure to give a light-yellow liquid. The liquid was partitioned between ethyl acetate and a saturated sodium bicarbonate solution. The ethyl acetate layer was washed with water and brine, dried ($MgSO_4$), and concentrated under reduced pressure to give the title compound as a light-yellow oil.

Analysis: Calculated for $C_{10}H_{12}ClNO$: C, 60.76; H, 6.12; N, 7.09. Found: C, 60.55; H, 6.02; N, 6.88.

PREPARATION 8

N-(3-Chloropropyl)-N-methylbenzenamine ethanedioate (1:1) hemihydrate

A solution of 5.4 g (0.050 mole) of N-methylaniline in 50 ml of dry (freshly distilled from lithium aluminum hydride) tetrahydrofuran was cooled to −78° C. using a dry ice-acetone bath while stirring under a nitrogen atmosphere. Via a syringe, 20 ml (0.050 mole) of 2.5M solution of n-butyllithium was added in a slow stream. The mixture was stirred at −78° C. for 30 min whereupon a precipitate formed. Via a syringe, a solution of 8.7 g (0.055 mole) of 1-bromo-3-chloropropane in 25 ml of dry tetrahydrofuran was added in a stream. The reaction mixture was then slowly warmed to ambient temperature whereupon the precipitate disappeared. The mixture was concentrated under reduced pressure and the residue partitioned between methylene chloride and a saturated sodium bicarbonate solution. The methylene chloride layer was washed with water and brine, dried ($MgSO_4$), and concentrated under reduced pressure to yield 8.8 g (96%) of yellow liquid. An analytical sample was prepared by purifying the oil by column chromatography using 100 g of silica gel on a 60 cm×3.5 cm column, eluted with ethyl acetate-hexane (1:100). The fractions containing the desired product were combined and concentrated under reduced pressure to give a liquid. The liquid was converted to the oxalic acid salt and the solid was recrystallized from 2-propanol/isopropyl ether to give white solid, mp 71°-73° C.

Analysis: Calc. for $C_{12}H_{16}ClNO_4 \cdot 0.5H_2O$: C, 50.98; H, 6.06; N, 4.95. Found: C, 51.27; H, 5.75; N, 4.90.

PREPARATION 9

4-Chloro-N-phenylbutanamide

A solution of 27.9 g (0.30 mole) of aniline in 100 ml of tetrahydrofuran was added dropwise to a solution of 21.2 g (0.15 mole) of 4-chlorobutyryl chloride in 100 ml of tetrahydrofuran. The reaction mixture was stirred mechanically and the temperature maintained between 5° C. and 15° C. throughout the addition. After the final addition, the solution was filtered to remove solid precipitates and the filtrate was concentrated under reduced pressure to yield 28.9 g (100%) of yellow solid. An analytical sample was prepared by recrystallizing the solid from benzene/petroleum ether (30°-60° C.) to give a white solid, mp 64°-66° C.

Analysis: Calculated for $C_{10}H_{12}ClNO$: C, 60.77; H, 6.12; N, 7.09. Found: C, 60.68; H, 6.16; N, 7.06.

PREPARATION 10

4-Chloro-N,N-diphenylbutanamide

A solution 22.8 g (0.14 mole) of diphenylamine in 150 ml of tetrahydrofuran was added dropwise to a solution of 9.9 g (0.07 mole) of 4-chlorobutyryl chloride in 100 ml of tetrahydrofuran. The reaction mixture was stirred mechanically and the temperature maintained between 5° C. and 15° C. throughout the addition. After the final addition, the solution was filtered to remove solid precipitates and the filtrate was concentrated under reduced pressure to give a yellow solid. The solid was purified by column chromatography using 300 g of silica gel on a 65 cm×4 cm column, eluted with 10% ethyl acetate in hexane. The fractions containing the desired product were combined and concentrated under reduced pressure to yield 16.8 g (88%) of white, crystalline solid, mp 78°-79° C.

Analysis: Calculated for $C_{16}H_{16}ClNO$: C, 70.20; H, 5.89; N, 5.12. Found: C, 70.28; H, 5.91; N, 5.12.

PREPARATION 11

4-Chloro-N,N-dimethylbutanamide

A solution of 50.0 g (1.11 mole) of dimethylamine in 100 ml of tetrahydrofuran was added dropwise to a solution of 28.2 (0.20 mole) of 4-chlorobutyryl chloride in 50 ml of tetrahydrofuran. The reaction mixture was stirred mechanically while the temperature was maintained between 5° C. and 15° C. throughout the addition. After the final addition, the solution was filtered to remove solid precipitates, and the filtrate concentrated under reduced pressure to yield 29.6 g (99%) of a yellow liquid. An analytical sample was prepared by filtering the liquid through a small bed of silica gel and eluting with ethyl acetate-hexane (1:1). The fractions containing the desired product were combined and concentrated under reduced pressure to give the title compound as a light-yellow liquid.

Analysis: Calculated for $C_6H_{12}ClNO$: C, 48.17; H, 8.08; N, 9.36. Found: C, 48.16; H, 8.12; N, 9.01.

PREPARATION 12

4-Chlorobutanamide

A solution of 50.3 g (0.36 mole) of 4-chlorobutyryl chloride in 300 ml of tetrahydrofuran was cooled to −78° C. using a dry ice-acetone bath. While stirring mechanically, gaseous ammonia was bubbled into the solution until saturated (∼20 min.). The reaction mixture was then allowed to slowly warm to ambient temperature, filtered to remove solid precipitates, and the filtrate was concentrated under reduced pressure. The residue was partitioned between chloroform and water. The chloroform layer was washed with water and brine, dried (MgSO₄) and concentrated under reduced pressure to give a solid. The solid was recrystallized from benzene/petroleum ether (30°-60° C.) to yield 7.3 g (17%) of white solid, mp 96°-98° C.

Analysis: Calculated for $C_4H_8ClNO$: C, 39.52; H, 6.63; N, 11.52. Found: C, 39.51; H, 6.75; N, 11.12.

PREPARATION 13

3-Chloropropanamide

A solution of 75.0 g (0.60 mole) of 3-chloropropionyl chloride in 500 ml of tetrahydrofuran was cooled to −78° C. using a dry ice-acetone bath. While stirring vigorously, gaseous ammonia was bubbled into the solution until saturated (∼20 min). The reaction mixture was then allowed to slowly warm to ambient temperature, filtered to remove solid precipitates, and the filtrate was concentrated under reduced pressure to yield 67.2 g (100%) of white solid. An analytical sample, mp 97°-100° C., was prepared from tetrahydrofuran.

Analysis: Calculated for $C_3H_6ClNO$: C, 33.651; H, 5.62; N, 13.03. Found: C, 33.57; H, 5.78; N, 12.95.

PREPARATION 14

5-Chloro-N-methylpentanamide

A mechanically stirred solution of 20.0 g (0.129 mole) of 5-chlorovaleryl chloride in 200 ml of tetrahydrofuran was cooled to 0°-5° C. using an ice bath, and gaseous monomethylamine was bubbled into the solution until saturated (∼10 min.). The reaction mixture was warmed to ambient temperature, filtered, and the filtrate concentrated under reduced pressure to yield 19.6 g (100%) of a golden oil. An analytical sample was prepared by filtering the oil through a small bed of silica gel and eluting with ethyl acetate. The fractions containing the desired product were combined and concentrated to give a light-yellow oil.

Analysis: Calculated for $C_6H_{12}ClNO$: C, 48.17; H, 8.08; N, 9.36. Found: C, 48.09; H, 8.49; N, 9.21.

PREPARATION 15

Methylphenylcarbamoyl chloride

A vigorously stirred solution of 10.7 g (0.1 mole) of N-methylaniline in 100 ml of acetonitrile was added dropwise under a nitrogen atmosphere to a cold mixture of 155 ml (0.3 mole) of a 1.93M solution of phosgene in toluene and 83.0 g (0.6 mole) of anhydrous potassium carbonate in 200 ml of acetonitrile. After the final addition, the mixture was stirred at ambient temperature for 16 h, filtered, and the filtrate concentrated under reduced pressure. The residue was recrystallized from benzene/petroleum ether (60°-110° C.) to yield 15.9 g (94%) of white solid, mp 85°-86° C.

Analysis: Calculated for $C_8H_8ClNO$: C, 56.65; H, 4.75; N, 8.26. Found: C, 56.37; H, 4.76; N, 8.27.

PREPARATION 16

6-Bromo-N,N-dimethylhexanamide

A solution of 27.5 g (0.610 mole) of dimethylamine in 100 ml of cold tetrahydrofuran was added dropwise to a solution of 25.0 g (0.117 mole) of 6-bromohexanoyl chloride in 100 ml of tetrahydrofuran. The reaction mixture was stirred mechanically and the temperature maintained between 5° and 15° C. throughout the addition. After the final addition, the solution was filtered to remove the solid precipitate and the filtrate was concentrated under reduced pressure to yield 23.3 g (90%) of light-yellow oil. An analytical sample was prepared by filtering the oil through a small bed of silica gel and eluting with ethyl acetate. The fractions containing the desired product were combined and concentrated under reduced pressure to give the title compound as a colorless oil.

Analysis: Calculated for $C_8H_{16}BrNO$: C, 43.26; H, 7.26; N, 6.31. Found: C, 43.24; H, 7.09; N, 6.62.

PREPARATION 17

1-Acetyl-α-(4-fluorophenyl)-α-phenyl-4-piperidinemethanol

A commercial (Alfa Inorganics) solution (667 ml, 2 mole) of phenylmagnesium bromide (3M in ethyl ether) was diluted with 2 L of anhydrous ethyl ether, cooled to 0°-10° C., and treated with a solution of 148 g (0.6 mole) of 1-acetyl-4-(4-fluorobenzoyl)piperidine (U.S. Pat. No. 3,576,810) in 1.5 L of anhydrous tetrahydrofuran dropwise over a 1.5 h period. The mixture was stirred at ambient temperature overnight and then poured into a solution of 107 g (2 mole) of ammonium chloride in 2 L of cold water. The mixture was extracted thrice with 1-L portions of benzene. The combined extracts were washed with water, dried (MgSO$_4$), and concentrated to give a semi-solid residue. The semi-solid was triturated with isopropyl ether and the mass crystallized. The solid was collected by filtration and dried to yield 87.8 g (45%) of white solid. An analytical sample, mp 173°–175° C., was prepared from 2-propanol.

Analysis: Calculated for C$_{20}$H$_{22}$FNO$_2$: C, 73.37; H, 6.77; N, 4.28. Found: C, 73.20; H, 6.93; N, 4.22.

PREPARATION 18

α-(4-fluorophenyl)-α-phenyl-4-piperidinemethanol

A mixture of 16.3 g (0.05 mole) of 1-acetyl-α-(4-fluorophenyl)-α-phenyl-4-piperidinemethanol and 5.6 g (0.1 mole) of potassium hydroxide in 150 ml of 95% ethanol and 20 ml of water was heated at reflux for 18 h. The mixture was poured into 1.5 L of ice-water and a solid precipitated. The solid was collected by filtration and dried. The gummy solid was dissolved in ethyl ether, filtered, and the filtrate slowly evaporated to 50 ml. The resulting solid was collected by filtration and recrystallized from 2-propanol/isopropyl ether to yield 3.5 g (25%) of white solid, mp 144.5°–146° C.

Analysis: Calculated for C$_{18}$H$_{20}$FNO: C, 75.76; H, 7.06; N, 4.91. Found: C, 75.91; H, 7.20; N, 4.93.

PREPARATION 19

α-(4-Fluorophenyl)-α-(4-piperidinyl)-2-pyridinemethanol

To a stirred solution of 36.3 g (0.23 mole) of 2-bromopyridine in 500 ml of anhydrous tetrahydrofuran (THF) at −65° C. was added 88 ml (0.22 mole) of a commercial solution of 2.5M n-butyllithium in hexane at such a rate that the temperature did not exceed −60° C. The dark solution was stirred at −65° C. for 1 h and then treated dropwise with a solution of 24.9 g (0.1 mole) of 1-acetyl-4-(4-fluorobenzoyl)piperidine in 250 ml of THF at such a rate that the temperature did not exceed −60° C. The mixture was stirred for 1 h at −65° C. and overnight at ambient temperature. The dark mixture was poured into 2 L of a saturated ammonium chloride solution. The layers were separated and the aqueous layer was extracted once with a 500-ml portion of methylene chloride. The combined organic layers were washed successively with 500 ml of water, 500 ml of a 4% sodium hydroxide solution, 250 ml of water, and 250 ml brine.

All of the combined aqueous layers were combined and allowed to stand in a filter flask for several weeks. As the soluble organic solvents in the aqueous solution evaporated, a solid precipitated. The aqueous solution was decanted and the solid was slurried with water, collected by filtration, and dried. The solid was recrystallized form absolute ethanol-pyridine to yield 4.5 g (14%) of off-white solid, mp 228°–230° C. (dec).

Analysis: Calculated for C$_{17}$H$_{19}$FN$_2$O: C, 71.31; H, 6.69; N, 9.78. Found: C, 71.43; H, 6.54; N, 9.52.

PREPARATION 20

α,α-Bis(3-fluorophenyl)-1-(phenylmethyl)-4-piperidinemethanol (E)-2-butanedioate (1:1)

A Grignard solution was prepared from 100 g (0.57 mole) of 1-bromo-3-fluorobenzene and 12.2 g (0.5 mole) of magnesium chips in 750 ml dry tetrahydrofuran (THF). The solution was treated with a solution of 45.8 g (0.185 mole) of ethyl N-benzylisonipecotate (U.S. Pat. No. 4,810,713) in 250 ml of dry THF, and the mixture was stirred at ambient temperature overnight. The solution was poured into 2.5 L of a saturated ammonium chloride solution, and the layers were separated. The aqueous layer was extracted once with 500 ml of methylene chloride (CH$_2$Cl$_2$) and twice with 250 ml of CH$_2$Cl$_2$. The combined organic layers were washed successively with 250 ml of water, 250 ml of a 4% sodium hydroxide solution, 250 ml of water, and 250 ml of brine, dried (Na$_2$SO$_4$) and concentrated to give a glass as residue. The glass was dissolved in 2-propanol and converted to the fumaric acid salt. The solid was collected by filtration and dried to yield 85 g (90%) of white solid. An analytical sample, mp 212°–214° C. (dec), was recrystallized from acetonitrile-water.

Analysis: Calculated for C$_{28}$H$_{29}$F$_2$NO$_5$: C, 68.36; H, 5.74; N, 2.75. Found: C, 68.46; H, 5.74; N, 2.83.

PREPARATION 21

α,α-Bis(3-fluorophenyl)-4-piperidinemethanol

A solution of 39.3 g (0.1 mol) of the base of α,α-bis(3-fluorophenyl)-1-(phenylmethyl)-4-piperidinemethanol in 750 ml of absolute ethanol was hydrogenated over 1 tsp of 5% Pd/C in a Parr apparatus at 50 psi and 60° C. for 3.5 days. The mixture was cooled and filtered through Celite®. The filtrate was concentrated, and the residue was dissolved in ethyl ether and filtered through cotton to remove some insoluble material. The filtrate was concentrated to give a gum which crystallized when triturated with petroleum ether (30°–60° C.). The solid was collected by filtration and dried to yield 27.9 g (92%) of white solid. An analytical sample, mp 117°–118° C., was recrystallized from isopropyl ether/2-propanol.

Analysis: Calculated for C$_{18}$H$_{19}$F$_2$NO: C, 71.27; H, 6.31; N, 4.62. Found: C, 71.24; H, 6.27; N, 4.66.

PREPARATION 22

α,α-Diphenyl-1-(phenylmethyl)-4-piperidinemethanol

A Grignard solution was prepared by the addition of 94.2 g (0.6 mole) of bromobenzene in 250 ml of dry (freshly distilled from lithium aluminum hydride) tetrahydrofuran (THF) to a mixture of 12.5 g (0.5 mole) of magnesium chips in 500 ml of dry THF. After the addition was complete, the mixture was heated at reflux for 15 min to complete formation. To this Grignard reagent at ambient temperature, was added a solution of 44.2 g (0.179 mole) of 1-(phenylmethyl)-4-piperidinecarboxylic acid ethyl ester in 250 ml of THF in a stream. The solution was stirred overnight at ambient temperature and then poured into 2.5 L of a saturated ammonium chloride solution. The layers were separated and the aqueous layer was extracted once with 500 ml of methylene chloride and twice with 250 ml of methylene chloride. The combined organic layers were washed successively with 500 ml of water, 750 ml of a 3% sodium hydroxide solution, 250 ml of water and 250 ml of brine. The organic layer was dried (Na$_2$SO$_4$) and concentrated to give a gum as residue. The gum was dissolved in 500 ml of ethyl ether, treated with activated charcoal, filtered through Celite®, and then concentrated to give a gum as residue. The gum crystallized when triturated with petroleum ether (30°–60° C.). The solid was collected by filtration and dried to yield 49.0 g (77%) of white solid. An analytical sample, mp 89.5°-90.5° C., was prepared from 2-propanol.

Analysis: Calculated for $C_{25}H_{27}NO$: C, 83.99; H, 7.61; N, 3.92. Found: C, 84.09; H, 7.63; N, 3.97.

PREPARATION 23

α,α-Diphenyl-4-piperidinemethanol

A mixture of 35.8 g (0.1 mole) of α,α-diphenyl-1-(phenylmethyl)-4-piperidinemethanol and 1 tsp of 5% Pd/C in 500 ml of absolute ethanol was hydrogenated at 60° C. in a Parr apparatus for 3 days. The mixture was filtered through Celite ® and the filtrate was concentrated to give a solid residue. The solid was triturated with petroleum ether (30°-60° C.), collected by filtration and dried to give 26.7 g (quantitative) of white solid. An analytical sample, mp 160°-161° C., was prepared from 2-propanol-isopropyl ether.

Analysis: Calculated for $C_{18}H_{21}NO$: C, 80.86; H, 7.92; N, 5.24. Found: C, 80.98; H, 7.96; N, 5.30.

PREPARATION 24

α,α-Bis(4-methylphenyl)-1-(phenylmethyl)-4-piperidinemethanol

A Grignard solution was prepared by the addition of 102.6 g (0.6 mole) of 4-bromotoluene in 500 ml of dry tetrahydrofuran (THF) to a mixture of 12.5 g (0.5 mole) of magnesium chips in 250 ml of THF. After the addition was complete, the mixture was heated at reflux for 1 h to complete formation. To this Grignard reagent at ambient temperature was added in a stream 42.9 g (0.173 mole) of 1-(phenylmethyl)-4-piperidinecarboxylic acid ethyl ester in 250 ml of dry THF. The solution was stirred at ambient temperature overnight and then poured into 2.5 L of a saturated ammonium chloride solution. The layers were separated and the aqueous layer was extracted twice with 375 ml portions of methylene chloride. The combined organic layers were washed successively with 500 ml of water, 750 ml of a 3% sodium hydroxide solution, 250 ml of water and 250 ml of brine. The organic layer was dried over sodium sulfate and concentrated under reduced pressure to give a gum as residue. The gum gradually crystallized. The solid was triturated with petroleum ether (30°-60° C.), collected by filtration and dried to yield 63.6 g (95%) of white solid. An analytical sample, mp 115°-117° C., was prepared from 2-propanol.

Analysis: Calculated for $C_{27}H_{31}NO$: C, 84.11; H, 8.10; N, 3.63. Found: C, 84.23; H, 8.13; N, 3.66.

PREPARATION 25

α,α-Bis(4-methylphenyl)-4-piperidinemethanol

A solution of 38.5 g (0.1 mole) of α,α-bis(4-methylphenyl)-1-(phenylmethyl)-4-piperidinemethanol in 500 ml of absolute ethanol was hydrogenated at 50 psi and 60° C. over 1 tsp of 5% palladium on carbon in a Parr apparatus for 3 days. The cooled mixture was filtered through Celite ® and the filtrate was concentrated under reduced pressure to give a glass as residue. The glass was crystallized from 2-propanol to yield 17.7 g (60%) of the title compound as a white solid, mp 150°-153° C.

Analysis: Calculated for $C_{20}H_{25}NO$: C, 81.31; H, 8.53; N, 4.74. Found: C, 81.18; H, 8.62; N, 4.72.

PREPARATION 26

α,α-Bis(4-methoxyphenyl)-1-(phenylmethyl)-4-piperidinemethanol ethanedioate (1:1) hemihydrate ethanol (2:1)

A Grignard reagent was prepared by the addition of a solution of 112.2 g (0.6 mole) of 4-bromoanisole in 500 ml of dry tetrahydrofuran (THF) to a mixture of 12.5 g (0.5 mole) of magnesium chips in 250 ml of THF. After the addition was complete, the mixture was heated at reflux for 0.5 h to complete formation. To this Grignard reagent at ambient temperature was added a solution of 42.8 g (0.173 mole) of 1-(phenylmethyl)-4-piperidinecarboxylic acid ethyl ester in 250 ml of THF in a stream. The mixture was stirred at ambient temperature overnight and then poured into 2.5 L of a saturated ammonium chloride solution. The layers were separated and the aqueous layer was extracted twice with 375 ml portions of methylene chloride. The combined organic layers were washed successively with 500 ml of water, 750 ml of a 3% sodium hydroxide solution, 250 ml of water and 250 ml of brine. The organic layer was dried over sodium sulfate and concentrated under reduced pressure to give a gum as residue. The gum was dissolved in 2-propanol and converted to the oxalic acid salt. The solid was collected by filtration, washed with 2-propanol and ethyl ether, and dried to yield 84.8 g (97%) of the title compound as a white power. An analytical sample, mp 128°-131° C. (dec) (slow heating; rapid heating gives mp ~110° C.), was prepared from absolute ethanol.

Analysis: Calculated for $C_{29}H_{33}NO_7 \cdot 0.5C_2H_5OH \cdot 0.5H_2O$: C, 66.74; H, 6.91; N, 2.60. Found: C, 67.08; H, 6.77; N, 2.67.

PREPARATION 27

α,α-Bis(4-methoxyphenyl)-4-piperidinemethanol

A solution of 36.7 g (0.088 mole) of α,α-bis(4-methoxyphenyl)-1-(phenylmethyl)-4-piperidinemethanol in 500 ml of absolute ethanol was hydrogenated over 1 tsp of 5% Pd/C at 60° C. in a Parr apparatus over the weekend. The mixture was cooled, filtered through Celite ®, fresh catalyst added to the filtrate and the process repeated until no starting material was present by mass spectral analysis. The filtrate was concentrated and the residue was partitioned between methylene chloride and a 5% sodium hydroxide solution. The organic layer was dried over sodium sulfate and concentrated to give a solid residue. The solid was recrystallized from 2-propanol to yield 8.6 g (30%) of white solid, mp 153°-155° C.

Analysis: Calculated for $C_{20}H_{25}NO_3$: C, 73.37; H, 7.70; N, 4.28. Found: C, 73.42; H, 7.72; N, 4.30.

PREPARATION 28

4-[Bis(3,4-difluorophenyl)methyl]pyridine

A mechanically stirred mixture of 49.0 g (0.43 mole) of 1,2-difluorobenzene, 20.6 g (0.19 mole) of pyridine-4-carboxaldehyde and 80 ml of concentrated $H_2SO_4$ was heated at 70° C. for 21 hours. The reaction mixture was poured over ice, and the icy mixture was made basic with 50% NaOH. The resulting mixture was extracted with $CH_2Cl_2$ and the $CH_2Cl_2$ solution was dried ($MgSO_4$). The solvent was removed in vacuo to give 54.94 g (89.8%) of a solid. This was recrystallized from a mixture of $CH_2Cl_2$ and hexane to give 44.82 g (74.3%)

of a crystalline solid, mp 79°-82° C. Proton NMR showed that this sample contained ~5% of the 2,3-difluoro isomer.

Analysis: Calculated for $C_{18}H_{11}F_4N$: C, 68.14; H, 3.50; N, 4.14. Found: C, 68.14; H, 3.36; N, 4.46.

PREPARATION 29

α,α-Bis(3,4-difluorophenyl)-4-pyridinemethanol

A solution of 5.66 g (0.0179 mole) of 4-[bis(3,4-difluorophenyl)methyl]pyridine and 12 drops of 50% NaOH in 50 ml of DMSO was stirred at room temperature for 4.5 h with air bubbling through the reaction mixture. Water was added to the solution, and a tan precipitate was collected. This was recrystallized from $CH_2Cl_2$-hexane to give 4.75 g (79.9%) of the title compound as a white, crystalline solid, mp 147°-149° C.

Analysis: Calculated for $C_{18}H_{11}F_4NO$: C, 64.87; H, 3.33; N, 4.20. Found: C, 64.54; H, 3.22; N, 4.20.

PREPARATION 30

α,α-Bis(3,4-Difluorophenyl)-4-piperidinemethanol ethanedioate hydrate (2:1:1)

A solution of 4.02 g (0.012 mole) of α,α-bis(3,4-difluorophenyl)-4-pyridinemethanol in 150 ml of glacial acetic acid was subjected to catalytic hydrogenation with 0.70 g of 5% Pt on carbon (Paar hydrogenation aparatus; 53 psi of $H_2$) at room temperature for 70 h. The solution was filtered through Celite®, and the solvent was removed in vacuo.

The residue was partitioned between $CH_2Cl_2$ and dilute NaOH, and the $CH_2Cl_2$ solution was dried ($Na_2SO_4$). The solvent was removed in vacuo to give a white solid. This was dissolved in $CH_3OH$, 1.0 g (0.011 mole) of oxalic acid was added, and anhydrous ether was added. After being cooled in the freezer, the solution produced 0.51 g (10.9%) of white crystalline solid. Anhydrous ether was added to the filtrate, and the solution was placed in the freezer. An additional 2.70 g (57.3%) of the title compound was collected as a white solid, mp 278°-279° C. dec.

Analysis: Calculated for $C_{18}H_{17}F_4NO\cdot 0.5C_2H_2O_4\cdot 0.5H_2O$: C, 58.02; H, 4.87; N, 3.56. Found: C, 58.42; H, 4.66; N, 3.61.

PREPARATION 31

4-[Bis(4-Chlorophenyl)hydroxymethyl]-N,N-diethyl-1-piperidinecarboxamide

A Grignard solution was prepared by the treatment of a slurry of 8.5 g (0.35 mole) of magnesium chips in 200 ml of dry tetrahydrofuran (THF) with a solution of 72.8 g (0.38 mole) of 1-bromo-4-chlorobenzene in 400 ml of THF. After the addition was complete, the mixture was heated at reflux for 15 min to complete formation. To the Grignard solution at ambient temperature was added a solution of 38.4 g (0.15 mole) of 1-[(diethylamino)carbonyl]-4-piperidine-carboxylic acid ethyl ester (J. Med. Chem. 1989 32(1), 105-118) in 200 ml of THF in a stream. The solution was stirred at ambient temperature overnight and poured into 2.5 L of a saturated ammonium chloride solution. The layers were separated and the aqueous layer was extracted once with 500 ml of methylene chloride and once with 250 ml of methylene chloride. The combined organic layers were filtered through Celite® and the filtrate was washed successively with 500 ml of water, 750 ml of a 4% sodium hydroxide solution, 250 ml of water and 250 ml of brine. The solution was dried ($Na_2SO_4$) and concentrated under reduced pressure to give a gum which gradually crystallized. The solid was triturated with petroleum ether (30°-60° C.), collected by filtration, and dried to yield 56.7 g (87%) of white solid. An analytical sample, mp 172°-175° C., was prepared from 2-propanol.

Analysis: Calculated for $C_{23}H_{28}Cl_2N_2O_2$: C, 63.54; H, 6.48; N, 6.43. Found: C, 63.60; H, 6.64; N, 6.25.

PREPARATION 32

α,α-Bis(4-chlorophenyl)-4-piperidinemethanol

To a slurry of 8.5 g (0.225 mole) of lithium aluminum hydride in 400 ml of anhydrous tetrahydrofuran (THF) was added a solution of 39.2 g (0.09 mole) of 4-[bis(4-chlorophenyl)hydroxymethyl]-N,N-diethyl-1-piperidinecarboxamide in 400 ml of THF in a stream over a 15 min period. The mixture was heated at reflux for 24 h, cooled, and treated successively with 8.5 ml of water, 25 ml of a 3N sodium hydroxide solution and 8.5 ml of water. The mixture was stirred for 0.5 h and then filtered. The filtrate was concentrated under reduced pressure to give a gum which crystallized. The solid was triturated with petroleum ether (30°-60° C.), collected by filtration and recrystallized from benzene to yield 10.5 g (35%) of white solid. An analytical sample, mp 184°-188° C., was prepared from 2-propanol.

Analysis: Calculated for $C_{18}H_{19}Cl_2NO$: C, 64.30; H, 5.70; N, 4.17. Found: C, 64.59; H, 5.79; N, 4.16.

EXAMPLE 1

4-[Bis(4-fluorophenyl)hydroxymethyl]-1-piperidineacetamide compound with ethoxyethane A mixture of 15.2 g (0.05 mole) of α,α-bis(4-fluorophenyl)-4-piperidinemethanol (U.S. Pat. No. 3,956,296), 5.1 g (0.055 mole) of 1-chloroacetamide, 15.9 g (0.15 mole) of anhydrous sodium carbonate and 0.4 g of potassium iodide in 150 ml of dimethylformamide was heated on a steam bath for 22 h. The mixture was poured into 1.5 L of water and a gum precipitated which crystallized upon standing overnight. The solid was collected by filtration, washed with water, dried, and recrystallized from 2-propanol/petroleum ether (30°-60° C.) to yield 11.7 g (65%) of the amide as an off-white solid. An analytical sample, mp 117°-119° C. (dec), was prepared from benzene-ethyl ether.

Analysis: Calc. for $C_{20}H_{22}F_2N_2O_2\cdot 0.5(CH_3CH_2)_2O$: C, 66.48; H, 6.85; N, 7.05. Found: C, 66.71; H, 6.87; N, 7.03.

EXAMPLE 2

4-[Bis(4-fluorophenyl)hydroxymethyl]-1-piperidinepropanamide

A mixture of 15.2 g (0.05 mole) of α,α-bis(4-fluorophenyl)-4-piperidinemethanol, 5.9 g (0.055 mole) of 3-chloropropionamide (Aldrich), 15.9 g (0.15 mole) of anhydrous sodium bicarbonate and 0.4 g of potassium iodide in 150 ml of dimethylformamide was heated on a steam bath for 24 h. The mixture was poured into 1.5 L of water and a solid precipitated. After standing overnight, the solid was collected by filtration, washed with water, dried, and recrystallized from benzene to yield 13.9 g (74%) of white solid, mp 136°-137° C.

Analysis: Calculated for $C_{21}H_{24}F_2N_2O_2$: C, 67.36; H, 6.46; N, 7.48. Found: C, 67.29; H, 6.40; N, 7.44.

EXAMPLE 3

4-[Bis(4-fluorophenyl)hydroxymethyl]-N-methyl-1-piperidinebutanamide

A mixture of 15.0 g (0.05 mole) of α,α-bis(4-fluorophenyl)-4-piperidinemethanol, 14.0 g (0.10 mole) of 4-chloro-N-methylbutanamide, 30.0 g (0.28 mole) of anhydrous sodium carbonate and 0.5 g (0.003 mole) of potassium iodide in 240 ml of 1-butanol was heated at reflux for 16 h. The mixture was concentrated under reduced pressure, and the residue partitioned between 250 ml of water and 250 ml of ethyl acetate. The ethyl acetate layer was washed with water and brine, dried (MgSO$_4$) and concentrated under reduced pressure to give a viscous oil. The oil was purified by column chromatography using 500 g of silica gel on a 110 cm × 5 cm column, eluted with 10% methanol in methylene chloride. The fractions containing the desired product were combined and concentrated under reduced pressure to yield 3.7 g (18%) of a white solid. An analytical sample was prepared by partitioning the solid between methylene chloride and 15% sodium hydroxide. The methylene chloride layer was washed with water and brine, dried (MgSO$_4$) and concentrated under reduced pressure to give a white solid which contained a small amount of CH$_2$Cl$_2$, mp 70°–72° C.

Analysis: Calculated for C$_{23}$H$_{28}$F$_2$N$_2$O$_2$: C, 68.64; H, 7.01; N, 6.96. Found: C, 67.92; H, 7.00; N, 6.82. Calc. for C$_{23}$H$_{28}$F$_2$N$_2$O$_2$.0.5Ch$_2$Cl$_2$: C, 68.07; H, 7.00; N, 6.82.

EXAMPLE 4

4-[Bis(4-fluorophenyl)hydroxymethyl]-N-phenyl-1-piperidinepropanamide

A mixture of 2.0 g (0.007 mole) of α,α-bis(4-fluorophenyl)-4-piperidinemethanol, 2.6 g (0.014 mole) of 3-chloro-N-phenylpropanamide, 8.5 g (0.080 mole) of anhydrous sodium carbonate and 0.3 g (0.002 mole) of potassium iodide in 50 ml of N,N-dimethylformamide was heated on a steam bath for 16 hours. The mixture was poured into 500 ml of water and extracted twice with 250 ml portions of ethyl acetate. The combined extracts were washed with water and brine, dried (MgSO$_4$) and concentrated under reduced pressure to give an off-white solid. The solid was recrystallized from methanol/2-propanol to yield 1.9 g (59%) of white solid, mp 190°–192° C.

Analysis: Calculated for C$_{27}$H$_{28}$F$_2$N$_2$O$_2$: C, 71.98; H, 6.26; N, 6.22. Found: C, 72.04; H, 6.28; N, 6.23.

EXAMPLE 5

4-[Bis(4-fluorophenyl)hydroxymethyl]-N-methyl-1-piperidinepropanamide

A mixture of 5.0 g (0.017 mole) of α,α-bis(4-fluorophenyl)-4-piperidinemethanol, 3.0 g (0.025 mole) of 3-chloro-N-methylpropanamide, 15.0 g (0.142 mole) of anhydrous sodium carbonate and 0.3 g (0.002 mole) of potassium iodide in 100 ml of N,N-dimethylformamide was heated on a steam bath for 16 h. The mixture was poured into 1.5 L of water and extracted twice with 150 ml portions of ethyl acetate. The ethyl acetate fractions were combined, washed with water and brine, dried (MgSO$_4$) and concentrated under reduced pressure to give a dark oil. The oil was purified by column chromatography using 150 g of silica gel on a 60 cm × 3.5 cm column, eluted with 10% methanol in methylene chloride. The fractions containing the desired product were partitioned between 15% sodium hydroxide and methylene chloride. The methylene chloride layer was washed with water and brine, dried (MgSO$_4$) and concentrated under reduced pressure to give a glass. Upon trituration with petroleum ether (30°–60° C.), the glass solidified. The solid was recrystallized from ethyl acetate/petroleum ether (30°–60° C.) to yield 3.2 g (50%) of white solid, mp 127°–129° C.

Analysis: Calculated for C$_{22}$H$_{26}$F$_2$N$_2$O$_2$: C, 68.02; H, 6.75; N, 7.21. Found: C, 67.75; H, 6.77; N, 7.16.

EXAMPLE 6

4-[Bis(4-fluorophenyl)hydroxymethyl]-N,N-dimethyl-1-piperidinepentanamide ethanedioate (1:1)

A mixture of 7.0 g (0.023 mole) of α,α-bis(4-fluorophenyl)-4-piperidinemethanol, 4.8 g (0.028 mole) of 5-chloro-N,N-dimethylpentanamide, 9.8 g (0.092 mole) of anhydrous sodium carbonate and 0.3 g (0.008 mole) of potassium iodide in 100 ml of N,N-dimethylformamide was heated on a steam bath for 16 h. The mixture was poured into 1.5 L of water and extracted twice with 200 ml portions of ethyl acetate. The ethyl acetate fractions were combined, washed with water and brine, dried (MgSO$_4$) and concentrated under reduced pressure to give a viscous oil. The oil was purified by column chromatography using 250 g of silica gel on a 69 cm × 4 cm column, eluted with 10% methanol in methylene chloride. The fractions containing the desired product were combined and concentrated under reduced pressure to give a viscous oil. The oil was converted to the oxalic acid salt and the solid was recrystallized from 2-propanol to yield 6.2 g (52%) of white solid, mp 193°–195° C.

Analysis: Calculated for C$_{27}$H$_{34}$F$_2$N$_2$O$_6$: C, 62.30; H, 6.58; N, 5.38. Found: C, 62.33; H, 6.63; N, 5.35.

EXAMPLE 7

4-[Bis(4-fluorophenyl)hydroxymethyl]-1-piperidineacetic acid ethyl ester (E)-2-butenedioate (1:1)

A mixture of 4.6 g (0.015 mole) of α,α-bis(4-fluorophenyl)-4-piperidinemethanol, 2.5 g (0.015 mole) of ethyl bromoacetate, 6.4 g (0.061 mole) of anhydrous sodium carbonate and 0.3 g (0.002 mole) of potassium iodide in 50 ml of N,N-dimethylformamide was heated on a steam bath for 16 h. The mixture was poured into 1 L of water and extracted thrice with 250 ml portions of ethyl acetate. The combined organic extracts were washed with water and brine, dried (MgSO$_4$) and concentrated under reduced pressure to give 6.0 g of a dark oil. The oil was purified by high pressure liquid chromatography (Waters Associates Prep LC/System 500A; PrepPAK ® 500/silica; ethyl acetate-hexane 1:2; flow rate 200 ml/min). The fractions containing the desired product were combined and concentrated under reduced pressure to give a colorless oil. The oil was converted to the fumaric acid salt and the solid was recrystallized from 2-propanol to yield 4.7 g (62%) of white solid, mp 178°–180° C.

Analysis: Calculated for C$_{26}$H$_{29}$F$_2$NO$_7$: C, 61.78; H, 5.78; N, 2.77. Found: C, 61.87; H, 5.76; N, 2.82.

EXAMPLE 8

4-[Bis(4-fluorophenyl)hydroxymethyl]-1-piperidinepropanoic acid ethyl ester ethanedioate (1:1)

This compound was prepared according to the procedure of Example 7. A mixture of 4.6 g (0.015 mole) of α,α-bis(4-fluorophenyl)-4-piperidinemethanol, 2.7 g (0.015 mole) of ethyl 3-bromopropionate, 6.4 g (0.061 mole) of anhydrous sodium carbonate and 0.3 g (0.002 mole) of potassium iodide in 50 ml of N,N-dimethylformamide gave 6.1 g of a dark oil. The oil was converted to the oxalic acid salt and the solid was recrystallized from 2-propanol to yield 6.4 g (87%) of white solid, mp 160°–162° C.

Analysis: Calculated for $C_{25}H_{29}F_2NO_7$: C, 60.85; H, 5.92; N, 2.84. Found: C, 60.84; H, 6.23; N, 2.76.

EXAMPLE 9

4-[Bis(4-fluorophenyl)hydroxymethyl]-1-piperidinebutanoic acid ethyl ester ethanedioate (1:1)

This compound was prepared according to the procedure of Example 7. A mixture of 4.6 g (0.015 mole) of α,α-bis(4-fluorophenyl)-4-piperidinemethanol, 2.9 g (0.015 mole) of ethyl 4-bromobutyrate, 6.4 g (0.061 mole) of anhydrous sodium carbonate and 0.3 g (0.002 mole) of potassium iodide in 50 ml of N,N-dimethylformamide gave 7.2 g of a dark oil. The oil was converted to the oxalic acid salt and the solid was recrystallized from 2-propanol to yield 6.2 g (82%) of a white solid, mp 164°–166° C.

Analysis: Calculated for $C_{26}H_{31}F_2NO_7$: C, 61.53; H, 6.16; N, 2.76. Found: C, 61.32; H, 6.53; N, 2.62.

EXAMPLE 10

4-[Bis(4-fluorophenyl)hydroxymethyl]-1-piperidinepentanoic acid ethyl ester ethanedioate (1:1)

This compound was prepared according to the procedure in Example 7. A mixture of 4.6 g (0.015 mole) of α,α-bis(4-fluorophenyl)-4-piperidinemethanol, 3.2 g (0.015 mole) of ethyl 5-bromovalerate, 6.4 g (0.061 mole) of anhydrous sodium carbonate and 0.3 g (0.002 mole) of potassium iodide in 50 ml of N,N-dimethylformamide gave 6.8 g of a dark oil. The oil was converted to the oxalic acid salt and the solid was recrystallized from 2-propanol to yield 5.7 g (73%) of the title compound as a white solid, mp 162°–163° C.

Analysis: Calculated for $C_{27}H_{33}F_2NO_7$: C, 62.18; H, 6.38; N, 2.69. Found: C, 62.12; H, 6.41; N, 2.75.

EXAMPLE 11

4-[Bis(4-fluorophenyl)hydroxymethyl]-1-piperidineheptanoic acid ethyl ester

This compound was prepared according to the procedure used in Example 7. A mixture of 4.6 g (0.015 mole) of α,α-bis(4-fluorophenyl)-4-piperidinemethanol, 3.6 g (0.015 mole) of ethyl 7-bromoheptanoate, 6.4 g (0.061 mole) of anhydrous sodium carbonate and 0.3 g (0.002 mole) of potassium iodide in 50 ml of N,N-dimethylformamide gave 6.0 g of a dark oil. The oil was purified by high pressure liquid chromatography (Waters Associates Prep LC/System 500A; PrepPAK® 500/silica; ethyl acetate; flow rate 150 ml/min). The fractions containing the desired product were combined and concentrated under reduced pressure to yield 2.5 g (44%) of a viscous, yellow oil.

Analysis: Calculated for $C_{27}H_{35}F_2NO_3$: C, 70.56; H, 7.68; N, 3.05. Found: C, 70.22; H, 7.43; N, 3.21.

EXAMPLE 12

4-[Bis(4-fluorophenyl)hydroxymethyl]-1-piperidinehexanoic acid ethyl ester (E)-2-butenedioate (1:3)

This compound was prepared according to the procedure of Example 7. A mixture of 4.6 g (0.015 mole) of α,α-bis(4-fluorophenyl)-4-piperidine methanol, 3.4 g (0.015 mole) of ethyl 6-bromocaproate, 6.4 g (0.061 mole) of anhydrous sodium carbonate and 0.3 g (0.002 mole) of potassium iodide in 50 ml of N,N-dimethylformamide gave 7.1 g of a dark oil. The oil was converted to the fumaric acid salt and the solid was recrystallized from ethyl acetate to yield 5.8 g (49%) of white solid, mp 119°–122° C.

Analysis: Calculated for $C_{38}H_{45}F_2NO_{15}$: C, 57.20; H, 5.71; N, 1.77. Found: C, 57.12; H, 5.67; N, 1.71.

EXAMPLE 13

4-[Bis(4-fluorophenyl)hydroxymethyl]-1-piperidineoctanoic acid ethyl ester

This compound was prepared according to the procedure used in Example 7. A mixture of 4.6 g (0.015 mole) of α,α-bis(4-fluorophenyl)-4-piperidinemethanol, 3.8 g (0.015 mole) of ethyl 8-bromooctanoate, 6.4 g (0.061 mole) of anhydrous sodium carbonate and 0.3 g (0.002 mole) of potassium iodide in 50 ml of N,N-dimethylformamide gave 6.7 g of a dark oil. The oil was purified by high pressure liquid chromatography (Waters Associates Prep LC/System 500A; PrepPAK® 500/silica; ethyl acetate-hexane 2:1; flow rate 150 ml/min). The fractions containing the desired product were combined and concentrated under reduced pressure to yield 4.3 g (72%) of the title compound as a viscous, yellow oil.

Analysis: Calculated for $C_{28}H_{37}F_2NO_3$: C, 71.01; H, 7.88; N, 2.96. Found: C, 70.71; H, 7.87; N, 2.99.

EXAMPLE 14

4-[Bis(4-fluorophenyl)hydroxymethyl]-1-piperidinedecanoic acid ethyl ester

A solution of 4.4 g (0.018 mole) of 10-bromodecanoic acid, 3 ml of methane sulfonic acid, and 250 ml of absolute ethanol was heated at reflux for 2 h. The mixture was concentrated under reduced pressure and the residue partitioned between ethyl acetate and water. The organic layer was washed with water and brine, dried (MgSO$_4$) and concentrated under reduced pressure to yield 5.0 g (100%) of ethyl 10-bromodecanoate as a yellow oil. A mixture of 4.6 g (0.015 mole) of α,α-bis(4-fluorophenyl)-4-piperidinemethanol, 4.2 g (0.015 mole) of ethyl 10-bromodecanoate, 6.4 g (0.015 mole) of anhydrous sodium carbonate and 0.3 g (0.002 mole) of potassium iodide in 50 ml of N,N-dimethylformamide was heated on a steam bath fo 6 h. The mixture was poured into 1 L of water and extracted three times with 250 ml portions of ethyl acetate. The ethyl acetate extracts were combined, washed with water and brine, dried (MgSO$_4$) and concentrated under reduced pressure to give a dark oil. The oil was purified by high pressure liquid chromatography (Water Associates Prep LC/System 500A; PrepPAK® 500/silica; ethyl acetate-hexane 2:1; flow rate 150 ml/min). The fractions containing the desired product were combined and concentrated under reduced pressure to yield 4.5 g (60%) of the title compound as a golden, viscous oil.

Analysis: Calculated for $C_{30}H_{41}F_2NO_3$: C, 71.83; H, 8.24; N, 2.79. Found: C, 71.74; H, 8.32; N, 2.80.

EXAMPLE 15

4-[Bis(4-fluorophenyl)hydroxymethyl]-1-piperidinenonanoic acid ethyl ester

A solution of 2.8 g (0.012 mole) of 9-bromononanoic acid, 2 ml of methane sulfonic acid, and 150 ml of absolute ethanol was heated at reflux for 2 h. The mixture was concentrated under reduced pressure and the residue partitioned between ethyl acetate and water. The organic layer was washed with water and brine, dried (MgSO$_4$) and concentrated under reduced pressure to yield 3.0 g (96%) of ethyl 9-bromonanoate as a light-yellow liquid. A mixture of 3.4 g (0.011 mole) of α,α-bis(4-fluorophenyl)-4-piperidinemethanol, 3.0 g (0.011 mole) of ethyl 9-bromonanoate, 6.4 g (0.060 mole) of anhydrous sodium carbonate and 0.3 g (0.002 mole) of potassium iodide in 50 ml of N,N-dimethylformamide was heated on a steam bath for 16 h. The mixture was poured into 1 L of water and extracted three times with 250 ml portions of ethyl acetate. The ethyl acetate extracts were combined, washed with water and brine, dried (MgSO$_4$) and concentrated under reduced pressure to give a dark oil. The oil was purified by high pressure liquid chromatography (Waters Associates Prep LC/System 500A; PrepPAK ® 500/silica; ethyl acetate-hexane 1:1; flow rate 150 ml/min). The fractions containing the desired product were combined and concentrated under reduced pressure to yield 4.0 g (75%) of golden viscous oil containing 0.25 mole of H$_2$O.

Analysis: Calculated for C$_{29}$H$_{33}$F$_2$NO$_3$.0.25H$_2$O: C, 70.78; H, 8.09; N, 2.85. Found: C, 70.78; H, 8.09; N, 2.85.

EXAMPLE 16

4-[Bis(4-fluorophenyl)hydroxymethyl]-1-piperidinebutanoic acid monohydrochloride hemihydrate To a stirred solution of 8.2 g (0.020 mole) of 4-[bis(4-fluorophenyl)hydroxymethyl]-1-piperidinebutanoic acid ethyl ester in 300 ml of 95% ethanol was added a solution of 20.2 g (0.240 mole) of sodium bicarbonate in 250 ml of water, and the mixture was heated at reflux for 4 h under a nitrogen atmosphere. The solvent was evaporated under reduced pressure and the residue was partitioned between ethyl ether and water. The layers were separated, and the aqueous layer was further extracted with two 300 ml portions of ethyl ether. The aqueous layer pH was adjusted to 2 with concentrated hydrochloric acid, and the mixture as extracted with three 300 ml portions of ethyl acetate. The combined ethyl acetate extracts were washed with water and brine, dried (MgSO$_4$) and concentrated under reduced pressure to give the hydrochloric acid salt as a white solid. The solid was recrystallized from ethyl acetate to yield 4.2 g (48%) of white solid, mp 170°–173° C.

Analysis: Calculated for C$_{22}$H$_{26}$ClF$_2$NO$_3$.0.5H$_2$O: C, 60.76; H, 6.26; N, 3.22. Found: C, 61.05; H, 6.34; N, 3.05.

EXAMPLE 17

4-[Bis(4-fluorophenyl)hydroxymethyl]-1-piperidinepentanoic acid

To a stirred solution of 9.0 g (0.020 mole) of 4-[bis(4-fluorophenyl)hydroxymethyl]-1-piperidinepentanoic acid ethyl ester in 300 ml of 95% ethanol was added a solution of 21.0 g (0.250 mole) of sodium bicarbonate in 250 ml of water, and the mixture was heated at reflux for 6 h under a nitrogen atmosphere. The solvent was evaporated under reduced pressure and the residue was partitioned between ethyl ether and water (300 ml each). The layers were separated, and the aqueous layer was further extracted with three 300 ml portions of ethyl ether. The aqueous layer pH was adjusted to 6 with glacial acetic acid, whereupon a soid precipitate began to form. After standing for 16 h the crystals were collected by filtration, washed with water and recrystallized from benzene to yield 4.2 g (52%) of the title compound as a white solid, mp 105°–107° C.

Analysis: Calculated for C$_{23}$H$_{27}$F$_2$NO$_3$: C, 68.47; H, 6.75; N, 3.47. Found: C, 68.45; H, 6.97; N, 3.31.

EXAMPLE 18

4-[Bis(4-fluorophenyl)hydroxymethyl]-N,N-diphenyl-1-piperidinepropanamide

A mixture of 12.0 g (0.040 mole) of α,α-bis(4-fluorophenyl)-4-piperidine methanol, 10.3 g (0.040 mole) of 3-chloro-N,N-diphenylpropanamide, 17.0 g (0.160 mole) of anhydrous sodium carbonate and 0.3 g (0.002 mole) of potassium iodide in 100 ml of N,N-dimethylformamide was heated on a steam bath for 16 h. The mixture was poured into 2 L of water and a solid precipitated. After standing 3 h, the solid was collected by filtration, washed with water, dried and recrystallized from benzene-petroleum ether (30°–60° C.) to yield 18.7 g (90%) of a white solid, mp 160°–162° C.

Analysis: Calculated for C$_{33}$H$_{32}$F$_2$N$_2$O$_2$: C, 75.27; H, 6.13; N, 5.32. Found: C, 75.33; H, 6.17; N, 5.29.

EXAMPLE 19

4-[Bis(4-fluorophenyl)hydroxymethyl]-N-methyl-N-phenyl-1-piperidinepropanamide

A mixture of 10.0 g (0.033 mole) of α,α-bis(4-fluorophenyl)-4-piperidine-methanol, 6.5 g (0.033 mole) of 3-chloro-N-methyl-N-phenylpropanamide, 14.0 g (0.132 mole) of anhydrous sodium carbonate and 0.3 g (0.002 mole) of potassium iodide in 100 ml of N,N-dimethylformamide was heated on a steam bath for 16 h. The mixture was poured into 2 L of water and extracted three times with 500 mL portions of ethyl acetate. The ethyl acetate fractions were combined, washed with water and brine, dried (MgSO$_4$) and concentrated under reduced pressure to give a yellow glass. The glass was purified by column chromatography using 250 g of silica gel on a 65 cm × 4 column, eluted with ethyl acetate. The fractions containing the desired product were combined and concentrated under reduced pressure to yield 11.0 g (72%) of a white solid. A portion of this solid was recrystallized from ethyl ether to give a white solid, mp 73°–75° C.

Analysis: Calculated for C$_{28}$H$_{30}$F$_2$N$_2$O$_2$: C, 72.39; H, 6.51; N, 6.03. Found: C, 72.09; H, 6.50; N, 6.01.

EXAMPLE 20

4-[Bis(4-fluorophenyl)hydroxymethyl]-N,N-dimethyl-1-piperidinepropanamide

A mixture of 10.0 g (0.033 mole) of α,α-bis(4-fluorophenyl)-4-piperidinemethanol, 4.5 g (0.033 mole) of 3-chloro-N,N-dimethylpropanamide, 14.0 g (0.132 mole) of anhydrous sodium carbonate and 0.3 g (0.002 mole) of potassium iodide in 100 ml of N,N-dimethylformamide was heated on a steam bath for 16 h. The mixture was poured into 2 L of water and extracted three times with 500 ml portions of ethyl acetate. The ethyl acetate fractions were combined, washed with water and brine, dried (MgSO$_4$) and concentrated under reduced pressure to give a glass. Upon trituration with petroleum ether (30°–60° C.) the glass solidified to yield 13.2 g (100%) of a yellow solid. A portion of this solid was recrystallized from ethyl ether to give the title compound as a white solid, mp 134°–135° C.

Analysis: Calculated for C$_{23}$H$_{28}$F$_2$N$_2$O$_2$: C, 68.54; H, 7.01; N, 6.96. Found: C, 68.66; H, 7.04; N, 6.96.

EXAMPLE 21

4-[Bis(4-fluorophenyl)hydroxymethyl]-N,N-diphenyl-1-piperidinebutanamide monohydrochloride hemihydrate A mixture of 6.1 g (0.020 mole) of α,α-bis(4-fluorophenyl)-4-piperidinemethanol, 6.8 g (0.025 mole) of 4-chloro-N,N-diphenylbutanamide, 8.5 g (0.080 mole) of anhydrous sodium carbonate and 0.3 g (0.002 mole) of potassium iodide in 100 mL of N,N-dimethylformamide was heated on a steam bath for 16 h. The mixture was poured into 2 L of water and extracted thrice with 250 mL portions of ethyl acetate. The ethyl acetate fractions were combined, washed with water and brine, dried ($MgSO_4$) and concentrated under reduced pressure to give a viscous oil. The oil was purified by column chromatography using 250 g of silica gel on a 65 cm×4 cm column, eluted with ethyl acetate. The fractions containing the desired product were combined and concentrated under reduced pressure to give a glass. The glass was converted to the hydrochloric acid salt and the solid was recrystallized from ethyl acetate/ethyl ether to yield 3.3 g (29%) of white solid, mp 130°–132° C.

Analysis: Calculated for $C_{34}H_{34}F_2N_2O_2.HCl.0.5H_2O$: C, 69.67; H, 6.19; N, 4.78. Found: C, 69.49; H, 6.07; N, 4.80.

EXAMPLE 22

4-[Bis(4-fluorophenyl)hydroxymethyl]-N,N-dimethyl-1-piperidinebutanamide ethanedioate (2:3)

A mixture of 6.1 g (0.020 mole) of α,α-bis(4-fluorophenyl)-4-piperidinemethanol, 3.7 g (0.025 mole) of 4-chloro-N,N-dimethylbutanamide, 8.5 g (0.080 mole) of anhydrous sodium carbonate and 0.3 g (0.002 mole) of potassium iodide in 100 mL of N,N-dimethylformamide was heated on a steam bath for 16 h. The mixture was poured into 1.5 L of water and extracted thrice with 500 mL portions of ethyl acetate. The ethyl acetate fractions were combined, washed with water and brine, dried ($MgSO_4$), and concentrated under reduced pressure to give a viscous oil. The oil was purified by column chromatography using 300 g of silica gel on a 65 cm×4 cm column, eluted with methanol-methylene chloride (1:15). Fractions containing the desired product were combined and concentrated under reduced pressure to give a viscous oil. The oil was converted to the oxalic acid salt and the solid was recrystallized from 2-propanol/ethyl acetate to yield 1.6 g (16%) of the title compound as a white solid, mp 156°–158° C.

Analysis: Calc. for $C_{24}H_{30}F_2N_2O_2.1.5C_2H_2O_4$: C, 58.80; H, 6.03; N, 5.08. Found: C, 58.90; H, 6.11; N, 5.02.

EXAMPLE 23

4-[Bis(4-fluorophenyl)hydroxymethyl]-N-phenyl-1-piperidinebutanamide ethanedioate compound with 2-propanol (2:2:1)

A mixture of 6.1 g (0.020 mole) of α,α-bis(4-fluorophenyl)-4-piperidinemethanol, 4.8 g (0.024 mole) of 4-chloro-N-phenylbutanamide, 8.5 g (0.080 mole) of anhydrous sodium carbonate and 0.3 g (0.002 mole) of potassium iodide in 100 mL of N,N-dimethylformamide was heated on a steam bath for 16 h. The mixture was poured into 1 L of water and extracted thrice with 100 mL portions of ethyl acetate. The ethyl acetate fractions were combined, washed with water and brine, dried ($MgSO_4$) and concentrated under reduced pressure to give a viscous oil. The oil was purified by column chromatography using 250 g of silica gel on a 65 cm×4 cm column, eluted with 10% methanol in methylene chloride. The fractions containing the desired product were combined and concentrated under reduced pressure to give a foam. The foam was converted to the oxalic acid salt, and the solid was recrystallized from 2-propanol to yield 3.0 g (26%) of the title compound as a white solid, mp 145°–147° C.

Analysis: Calc. for $C_{28}H_{30}F_2N_2O_2.C_2H_2O_4.0.5C_3H_8O$: C, 64.72; H, 6.21; N, 4.79. Found: C, 64.55; H, 6.25; N, 5.00.

EXAMPLE 24

4-[Bis(4-fluorophenyl)hydroxymethyl]-N-methyl-N-phenyl-1-piperidinebutanamide hydrochloride hydrate (2:2:1)

A mixture of 6.1 g (0.020 mole) of α,α-bis(4-fluorophenyl)-4-piperidinemethanol, 6.4 g (0.030 mole) of 4-chloro-N-methyl-N-phenylbutanamide, 8.5 g (0.080 mole) of anhydrous sodium carbonate and 0.4 g (0.002 mole) of potassium iodide in 100 mL of N,N-dimethylformamide was stirred at ambient temperature for 72 h. The mixture was poured into 1.5 L of water and extracted thrice with 250 mL portions of ethyl acetate. The ethyl acetate fractions were combined, washed with water and brine, dried ($MgSO_4$), and concentrated under reduced pressure to give a dark oil. The oil was purified by column chromatography using 250 g of silica gel on a 65 cm×4 cm column eluted with 5% methanol in methylene chloride. The fractions containing the desired product were combined and concentrated under reduced pressure to give a glass. The glass was converted to the hydrochloric acid salt, and the solid was recrystallized from 2-propanol/isopropyl ether to yield 2.8 g (27%) of the title compound as a white solid, mp 107°–110° C.

Analysis: Calc. for $C_{29}H_{32}F_2N_2O_2.HCl.0.5H_2O$: C, 66.47; H, 6.54; N, 5.35. Found: C, 66.84; H, 6.47; N, 5.46.

EXAMPLE 25

4-[Bis(4-fluorophenyl)hydroxymethyl]-1-piperidinebutanamide ethanedioate (1:1)

A mixture of 6.1 g (0.020 mole) of α,α-bis(4-fluorophenyl)-4-piperidinemethanol, 4.9 g (0.040 mole) of 4-chlorobutanamide, 8.5 g (0.080 mole) of anhydrous sodium carbonate and 0.4 g (0.002 mole) of potassium iodide in 100 mL of N,N-dimethylformamide was stirred at ambient temperature for 24 h. The mixture was poured into 1.5 L of water and extracted twice with 500 mL portions of ethyl acetate. The ethyl acetate fractions were combined, washed with water and brine, dried ($MgSO_4$), and concentrated under reduced pressure to give a dark oil. The oil was purified by column chromatography using 250 g of silica gel on a 65 cm×4 cm column eluted with methanol-methylene chloride (1:2). The fractions containing the desired product were combined and concentrated under reduced pressure. The residue was partitioned between methylene chloride and water. The methylene chloride layer was washed with water and brine, dried ($MgSO_4$) and concentrated under reduced pressure to give a glass. The glass was converted to the oxalic acid salt, and the solid was recrystallized from ethyl acetate/2-propanol to yield 0.7 g (9%) of the title compound as a white solid containing 0.25 mole $H_2O$, mp 177°–179° C.

EXAMPLE 26

4-[Bis(4-fluorophenyl)hydroxymethyl]-1-piperidinebutanamide

A solution of 17.6 g (0.042 mole) of 4-[bis(4-fluorophenyl)hydroxymethyl]-1-piperidinebutanoic acid ethyl ester in 100 mL of 4:1 liquid ammonia/methanol was sealed in a 250 mL steel bomb and heated at 150° C. for 72 h. The solution was allowed to stand at ambient temperature for 24 h and water was added dropwise until a solid began to precipitate. The solid was collected by filtration, washed with water, and dried to yield 10.1 g (62%) of yellow solid. An analytical sample, mp 110°–113° C., was prepared from ethyl acetate/isopropyl ether as a white solid.

Analysis: Calculated for $C_{22}H_{26}F_2N_2O_2$: C, 68.02; H, 6.75; N, 7.21. Found: C, 67.63; H, 6.78; N, 7.15.

EXAMPLE 27

4-[Bis(4-fluorophenyl)hydroxymethyl]-N-methyl-1-piperidineacetamide

A mixture of 12.1 g (0.040 mole) of $\alpha,\alpha$-bis(4-fluorophenyl)-4-piperidinemethanol, 5.2 g (0.048 mole) of 2-chloro-N-methylacetamide, 17.0 g (0.160 mole) of anhydrous sodium carbonate and 0.4 g (0.002 mole) of potassium iodide in 100 mL of N,N-dimethylformamide was heated on a steam bath for 16 h. The mixture was poured into 1.5 L of water and extracted twice with 500 mL portions of ethyl acetate. The ethyl acetate layers were combined, washed with water and brine, dried (MgSO$_4$), and concentrated under reduced pressure. The residue was recrystallized from ethyl acetate to yield 14.2 g (95%) of white solid, mp 122°–124° C.

Analysis: Calculated for $C_{21}H_{24}F_2N_2O_2$: C, 67.36; H, 6.46; N, 7.48. Found: C, 67.32; H, 6.54; N, 7.36.

EXAMPLE 28

4-[Bis(4-fluorophenyl)hydroxymethyl]-N-methyl-1-piperidinepentanamide

A solution of 6.1 g (0.020 mole) of $\alpha,\alpha$-bis(4-fluorophenyl)-4-piperidinemethanol, 3.7 g (0.025 mole) of 5-chloro-N-methylpentanamide, 8.5 g (0.080 mole) of anhydrous sodium carbonate and 0.4 g (0.002 mole) of potassium iodide in 100 mL of N,N-dimethylformamide was heated on a steam bath for 24 h. The mixture was poured into 1.5 L of water and extracted twice with 500 ml portions of ethyl acetate. The ethyl acetate portions were combined, washed with water and brine, dried (MgSO$_4$) and concentrated under reduced pressure to give a golden oil. The oil was dissolved in ethyl ether and allowed to stand, whereupon a white solid precipitated. The solid was collected by filtration, and recrystallized from ethyl ether to yield 5.9 g (71%) of white solid, mp 130°–131° C.

Analysis: Calculated for $C_{24}H_{30}F_2N_2O_2$: C, 69.21; H, 7.26; N, 6.73. Found: C, 69.48; H, 7.40; N, 6.71.

EXAMPLE 29

4-[Bis(4-fluorophenyl)hydroxymethyl]-N,N-dimethyl-1-piperidinehexanamide ethanedioate (1:1)

A mixture of 4.0 g (0.013 mole) of $\alpha,\alpha$-bis(4-fluorophenyl)-4-piperidinemethanol, 3.5 g (0.016 mole) of 6-bromo-N,N-dimethylhexanamide, 5.5 g (0.052 mole) of anhydrous sodium carbonate and 0.3 g (0.002 mole) of potassium iodide in 50 mL of N,N-dimethylformamide was stirred at ambient temperature for 16 h. The mixture was poured into 1 L of water and extracted twice with 250 mL of ethyl acetate. The combined ethyl acetate fractions were washed with water and brine, dried (MgSO$_4$) and concentrated under reduced pressure. The residue was converted to the oxalic acid salt, and recrystallized from 2-propanol to yield 4.9 g (71%) of the title compound as a white solid, mp 157°–160° C.

Analysis: Calculated for $C_{26}H_{34}F_2N_2O_2.C_2H_2O_4$: C, 62.91; H, 6.79; N, 5.24. Found: C, 62.50; H, 6.87; N, 5.16.

EXAMPLE 30

4-[Bis(4-fluorophenyl)hydroxymethyl]-1-piperidineacetic acid hemihydrate

To a stirred solution of 5.0 g (0.013 mole) of 4-[bis(4-fluorophenyl)hydroxymethyl]-1-piperidineacetic acid ethyl ester in 100 mL of 95% ethanol was added a solution of 10.9 g (0.130 mole) of sodium bicarbonate in 150 mL of water and the mixture was heated at reflux for 16 h. The solution was cooled and concentrated under reduced pressure. The residue was partitioned between ethyl ether and water (200 mL each). The layers were separated, and the aqueous layer was further extracted with two 100 mL portions of ethyl ether. The aqueous layer pH was adjusted to 6 with glacial acetic acid, whereupon a solid precipitate began to form. After standing for 16 h, the crystals were collected by filtration, washed with water and recrystallized from 2-propanol to yield 1.7 g (36%) of white solid, mp 198°–200° C.

Analysis: Calculated for $C_{20}H_{21}F_2NO_3.0.5H_2O$: C, 64.86; H, 5.99; N, 3.78. Found: C, 65.19; H, 6.16; N, 3.76.

EXAMPLE 31

Following the procedure of Example 3 and substituting for $\alpha,\alpha$-bis(4-fluorophenyl)-4-piperidinemethanol the following intermediates:

a. $\alpha,\alpha$-diphenyl-4-piperidinemethanol
b. $\alpha,\alpha$-bis(4-methylphenyl)-4-piperidinemethanol
c. $\alpha,\alpha$-bis(4-methoxyphenyl)-4-piperidinemethanol
d. $\alpha,\alpha$-bis(4-chlorophenyl)-4-piperidinemethanol
e. $\alpha$-(4-fluorophenyl)-$\alpha$-phenyl-4-piperidinemethanol
f. $\alpha,\alpha$-bis(3,4-difluorophenyl)-4-piperidinemethanol
g. $\alpha,\alpha$-bis(3-fluorophenyl)-4-piperidinemethanol
h. $\alpha$-(4-fluorophenyl)-$\alpha$-(4-piperidinyl)-2-pyridinemethanol there are obtained respectively a. 4-(diphenylhydroxymethyl)-N-methyl-1-piperidinebutanamide
b. 4-[bis(4-methylphenyl)hydroxymethyl]-N-methyl-1-piperidinebutanamide
c. 4-[bis(4-methoxyphenyl)hydroxymethyl]-N-methyl-1-piperidinebutanamide
d. 4-[bis(4-chlorophenyl)hydroxymethyl]-N-methyl-1-piperidinebutanamide
e. 4-[(4-fluorophenyl)hydroxy(phenyl)methyl]-N-methyl-1-piperidinebutanamide
f. 4-[bis(3,4-difluorophenyl)hydroxymethyl]-N-methyl-1-piperidinebutanamide
g. 4-[bis(3-fluorophenyl)hydroxymethyl]-N-methyl-1-piperidinebutanamide
h. 4[(4-fluorophenyl)hydroxy(2-pyridinyl)methyl]-N-methyl-1-piperidinebutanamide.

EXAMPLE 32

Following the procedure of Example 5 and substituting for α,α-bis(4-fluorophenyl)-4-piperidine methanol the following intermediates:
a. α,α-diphenyl-4-piperidinemethanol
b. α,α-bis(4-methylphenyl)-4-piperidinemethanol
c. α,α-bis(4-methoxyphenyl)-4-piperidinemethanol
d. α,α-bis(4-chlorophenyl)-4-piperidinemethanol
e. α-(4-fluorophenyl)-α-phenyl-4-piperidinemethanol
f. α,α-bis(3,4-difluorophenyl)-4-piperidinemethanol
g. α,α-bis(3-fluorophenyl)-4-piperidinemethanol
h. α-(4-fluorophenyl)-α-(4-piperidinyl)-2-pyridinemethanol there are obtained respectively
a. 4-(diphenylhydroxymethyl)-N-methyl-1-piperidinepropanamide
b. 4-[bis(4-methylphenyl)hydroxymethyl]-N-methyl-1-piperidinepropanamide
c. 4-[bis(4-methoxyphenyl)hydroxymethyl]-N-methyl-1-piperidinepropanamide
d. 4-[bis(4-chlorophenyl)hydroxymethyl]-N-methyl-1-piperidinepropanamide
e. 4-[(4-fluorophenyl)hydroxy(phenyl)methyl]-N-methyl-1-piperidinebutanamide
f. 4-[bis(3,4-difluorophenyl)hydroxymethyl]-N-methyl-1-piperidinepropanamide
g. 4-[bis(3-fluorophenyl)hydroxymethyl]-N-methyl-1-piperidinepropanamide
h. 4-[(4-fluorophenyl)hydroxy(2-pyridinyl)methyl]-N-methyl-1-piperidinepropanamide.

EXAMPLE 33

Following the procedure of Example 6 and substituting for α,α-bis(4-fluorophenyl)-4-piperidine methanol the following intermediates:
a. α,α-diphenyl-4-piperidinemethanol
b. α,α-bis(4-methylphenyl)-4-piperidinemethanol
c. α,α-bis(4-methoxyphenyl)-4-piperidinemethanol
d. α,α-bis(4-chlorophenyl)-4-piperidinemethanol
e. α-(4-fluorophenyl)-α-phenyl-4-piperidinemethanol
f. α,α-bis(3,4-difluorophenyl)-4-piperidinemethanol
g. α,α-bis(3-fluorophenyl)-4-piperidinemethanol
h. α-(4-fluorophenyl)-α-(4-piperidinyl)-2-pyridinemethanol there are obtained respectively
a. 4-(diphenylhydroxymethyl)-N,N-dimethyl-1-piperidinepentanamide
b. 4-[bis(4-methylphenyl)hydroxymethyl]-N,N-dimethyl-1-piperidinepentanamide
c. 4-[bis(4-methoxyphenyl)hydroxymethyl]-N,N-dimethyl-1-piperidinepentanamide
d. 4-[bis(4-chlorophenyl)hydroxymethyl]-N,N-dimethyl-1-piperidinepentanamide
e. 4-[(4-fluorophenyl)hydroxy(phenyl)methyl]-N,N-dimethyl-1-piperidinepentanamide
f. 4-[bis(3,4-difluorophenyl)hydroxymethyl]-N,N-dimethyl-1-piperidinepentanamide
g. 4-[bis(3-fluorophenyl)hydroxymethyl]-N,N-dimethyl-1-piperidinepentanamdie
h. 4-[(4-fluorophenyl)hydroxy(2-pyridinyl)methyl]-N,N-dimethyl-1-piperidinepentanamide.

EXAMPLE 34

Following the procedure of Example 12 and substituting for α,α-bis(4-fluorophenyl)-4-piperidine methanol the following intermediates:
a. α,α-diphenyl-4-piperidinemethanol
b. α,α-bis(4-methylphenyl)-4-piperidinemethanol
c. α,α-bis(4-methoxyphenyl)-4-piperidinemethanol
d. α,α-bis(4-chlorophenyl)-4-piperidinemethanol
e. α-(4-fluorophenyl)-α-phenyl-4-piperidinemethanol
f. α,α-bis(3,4-difluorophenyl)-4-piperidinemethanol
g. α,α-bis(3-fluorophenyl)-4-piperidinemethanol
h. α-(4-fluorophenyl)-α-(4-piperidinyl)-2-pyridinemethanol there are obtained respectively
a. 4-(diphenylhydroxymethyl)-1-piperidinehexanoic acid ethyl ester.
b. 4-[bis(4-methylphenyl)hydroxymethyl]-1-piperidinehexanoic acid ethyl ester
c. 4-[bis(4-methoxyphenyl)hydroxymethyl]-1-piperidinehexanoic acid ethyl ester.
d. 4-[bis(4-chlorophenyl)hydroxymethyl]-1-piperidinehexanoic acid ethyl ester.
e. 4-[(4-fluorophenyl)hydroxy(phenyl)methyl]-1-piperidinehexanoic acid ethyl ester.
f. 4-[bis(3,4-difluorophenyl)hydroxymethyl]-1-piperidinehexanoic acid ethyl ester.
g. 4-[bis(3-fluorophenyl)hydroxymethyl]-1-piperidinehexanoic acid ethyl ester.
h. 4-[(4-fluorophenyl)hydroxy(2-pyridinyl)methyl]-1-piperidinehexanoic acid ethyl ester.

EXAMPLE 35

Following the procedure of Example 15 and substituting for α,α-bis(4-fluorophenyl)-4-piperidine methanol the following intermediates:
a. α,α-diphenyl-4-piperidinemethanol
b. α,α-bis(4-methylphenyl)-4-piperidinemethanol
c. α,α-bis(4-methoxyphenyl)-4-piperidinemethanol
d. α,α-bis(4-chlorophenyl)-4-piperidinemethanol
e. α-(4-fluorophenyl)-α-phenyl-4-piperidinemethanol
f. α,α-bis(3,4-difluorophenyl)-4-piperidinemethanol
g. α,α-bis(3-fluorophenyl)-4-piperidinemethanol
h. α-(4-fluorophenyl)-α-(4-piperidinyl)-2-pyridinemethanol there are obtained respectively
a. 4-(diphenylhydroxymethyl)-1-piperidinenonanoic acid ethyl ester.
b. 4-[bis(4-methylphenyl)hydroxymethyl]-1-piperidinenonanoic acid ethyl ester.
c. 4-[bis(4-methoxyphenyl)hydroxymethyl]-1-piperidinenonanoic acid ethyl ester.
d. 4-[bis(4-chlorophenyl)hydroxymethyl]-1-piperidinenonanoic acid ethyl ester.
e. 4-[(4-fluorophenyl)hydroxy(phenyl)methyl]-1-piperidinenonanoic acid ethyl ester.
f. 4-[bis(3,4-difluorophenyl)hydroxymethyl]-1-piperidinenonanoic acid ethyl ester.
g. 4-[bis(3-fluorophenyl)hydroxymethyl]-1-piperidinenonanoic acid ethyl ester.
h. 4-[(4-fluorophenyl)hydroxy(2-pyridinyl)methyl]-1-piperidinenonanoic acid ethyl ester.

EXAMPLE 36

Following the procedure of Example 22 and substituting for α,α-bis(4-fluorophenyl)-4-piperidine methanol the following intermediates:
a. α,α-diphenyl-4-piperidinemethanol
b. α,α-bis(4-methylphenyl)-4-piperidinemethanol
c. α,α-bis(4-methoxyphenyl)-4-piperidinemethanol
d. α,α-bis(4-chlorophenyl)-4-piperidinemethanol
e. α-(4-fluorophenyl)-α-phenyl-4-piperidinemethanol
f. α,α-bis(3,4-difluorophenyl)-4-piperidinemethanol
g. α,α-bis(3-fluorophenyl)-4-piperidinemethanol h. α-(4-fluorophenyl)-α-(4-piperidinyl)-2-pyridinemethanol there are obtained respectively
a. 4-(diphenylhydroxymethyl)-N,N-dimethyl-1-piperidinebutanamide.
b. 4[bis(4-methylphenyl)hydroxymethyl]-N,N-dimethyl-1-piperidinebutanamide.
c. 4-[bis(4-methoxyphenyl)hydroxymethyl]-N,N-dimethyl-1-piperidinebutanamide.
d. 4-[bis(4-chlorophenyl)hydroxymethyl]-N,N-dimethyl-1-piperidinebutanamide.
e. 4-[(4-fluorophenyl)hydroxy(phenyl)methyl]-N,N-dimethyl-1-piperidinebutanamide.
f. 4-[bis(3,4-difluorophenyl)hydroxymethyl]-N,N-dimethyl-1-piperidinebutanamide.
g. 4-[bis(3-fluorophenyl)hydroxymethyl]-N,N-dimethyl-1-piperidinebutanamide.
h. 4-[(4-fluorophenyl)hydroxy(2-pyridinyl)methyl]-N,N-dimethyl-1-piperidinebutanamide.

EXAMPLE 37

Following the procedure of Example 28 and substituting for α,α-bis(4-fluorophenyl)-4-piperidine methanol the following intermediates:
a. α,α-diphenyl-4-piperidinemethanol
b. α,α-bis(4-methylphenyl)-4-piperidinemethanol
c. α,α-bis(4-methoxyphenyl)-4-piperidinemethanol
d. α,α-bis(4-chlorophenyl)-4-piperidinemethanol
e. α-(4-fluorophenyl)-α-phenyl-4-piperidinemethanol
f. α,α-bis(3,4-difluorophenyl)-4-piperidinemethanol
g. α,α-bis(3-fluorophenyl)-4-piperidinemethanol
h. α-(4-fluorophenyl)-α-(4-piperidinyl)-2-pyridinemethanol there are obtained respectively
a. 4-(diphenylhydroxymethyl)-N-methyl-1-piperidinepentanamide.
b. 4-[bis(4-methylphenyl)hydroxymethyl]-N-methyl-1-piperidinepentanamide.
c. 4-[bis(4-methoxyphenyl)hydroxymethyl]-N-methyl-1-piperidinepentanamide.
d. 4-[bis(4-chlorophenyl)hydroxymethyl]-N-methyl-1-piperidinepentanamide.
e. 4-[(4-fluorophenyl)hydroxy(phenyl)methyl]-N-methyl-1-piperidinepentanamide.
f. 4-[bis(3,4-difluorophenyl)hydroxymethyl]-N-methyl-1-piperidinepentanamide.
g. 4-[bis(3-fluorophenyl)hydroxymethyl]-N-methyl-1-piperidinepentanamide.
h. 4-[(4-fluorophenyl)hydroxy(2-pyridinyl)methyl]-N-methyl-1-piperidinepentanamide.

EXAMPLE 38

Following the procedure of Example 29 and substituting for α,α-bis(4-fluorophenyl)-4-piperidine methanol the following intermediates:
a. α,α-diphenyl-4-piperidinemethanol
b. α,α-bis(4-methylphenyl)-4-piperidinemethanol
c. α,α-bis(4-methoxyphenyl)-4-piperidinemethanol
d. α,α-bis(4-chlorophenyl)-4-piperidinemethanol
e. α-(4-fluorophenyl)-α-phenyl-4-piperidinemethanol
f. α,α-bis(3,4-difluorophenyl)-4-piperidinemethanol
g. α,α-bis(3-fluorophenyl)-4-piperidinemethanol
h. α-(4-fluorophenyl)-α-(4-piperidinyl)-2-pyridinemethanol there are obtained respectively
a. 4-(diphenylhydroxymethyl)-N,N-dimethyl-1-piperidinehexanamide.
b. 4-[bis(4-methylphenyl)hydroxymethyl]-N,N-dimethyl-1-piperidinehexanamide.
c. 4-[bis(4-methoxyphenyl)hydroxymethyl]-N,N-dimethyl-1-piperidinehexanamide.
d. 4-[bis(4-chlorophenyl)hydroxymethyl]-N,N-dimethyl-1-piperidinehexanamide.
e. 4-[(4-fluorophenyl)hydroxy(phenyl)methyl]-N,N-dimethyl-1-piperidinehexanamide.
f. 4-[bis(3,4-difluorophenyl)hydroxymethyl]-N,N-dimethyl-1-piperidinehexanamide.
g. 4-[bis(3-fluorophenyl)hydroxymethyl]-N,N-dimethyl-1-piperidinehexanamide.
h. 4-[(4-fluorophenyl)hydroxy(2-pyridinyl)methyl]-N,N-dimethyl-1-piperidinehexanamide.

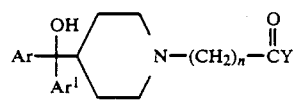

| Ex | Ar | Ar$^1$ | n | Y | Salt |
|---|---|---|---|---|---|
| 1 | 4-F—C$_6$H$_4$ | 4-F—C$_6$H$_4$— | 1 | NH$_2$ | 0.5(C$_2$H$_5$)$_2$O |
| 2 | 4-F—C$_6$H$_4$ | 4-F—C$_6$H$_4$— | 2 | NH$_2$ | — |
| 3 | 4-F—C$_6$H$_4$ | 4-F—C$_6$H$_4$— | 3 | NHCH$_3$ | — |
| 4 | 4-F—C$_6$H$_4$ | 4-F—C$_6$H$_4$— | 2 | NHC$_6$H$_5$ | — |
| 5 | 4-F—C$_6$H$_4$ | 4-F—C$_6$H$_4$— | 2 | NHCH$_3$ | — |
| 6 | 4-F—C$_6$H$_4$ | 4-F—C$_6$H$_4$— | 4 | N(CH$_3$)$_2$ | oxalate |
| 7 | 4-F—C$_6$H$_4$ | 4-F—C$_6$H$_4$— | 1 | OC$_2$H$_5$ | fumarate |
| 8 | 4-F—C$_6$H$_4$ | 4-F—C$_6$H$_4$— | 2 | OC$_2$H$_5$ | oxalate |
| 9 | 4-F—C$_6$H$_4$ | 4-F—C$_6$H$_4$— | 3 | OC$_2$H$_5$ | oxalate |
| 10 | 4-F—C$_6$H$_4$ | 4-F—C$_6$H$_4$— | 4 | OC$_2$H$_5$ | oxalate |
| 11 | 4-F—C$_6$H$_4$ | 4-F—C$_6$H$_4$— | 6 | OC$_2$H$_5$ | — |
| 12 | 4-F—C$_6$H$_4$ | 4-F—C$_6$H$_4$— | 5 | OC$_2$H$_5$ | fumarate |
| 13 | 4-F—C$_6$H$_4$ | 4-F—C$_6$H$_4$— | 7 | OC$_2$H$_5$ | — |
| 14 | 4-F—C$_6$H$_4$ | 4-F—C$_6$H$_4$— | 9 | OC$_2$H$_5$ | — |
| 15 | 4-F—C$_6$H$_4$ | 4-F—C$_6$H$_4$— | 8 | OC$_2$H$_5$ | — |
| 16 | 4-F—C$_6$H$_4$ | 4-F—C$_6$H$_4$— | 3 | OH | HCl.0.5H$_2$O |
| 17 | 4-F—C$_6$H$_4$ | 4-F—C$_6$H$_4$— | 4 | OH | — |
| 18 | 4-F—C$_6$H$_4$ | 4-F—C$_6$H$_4$— | 2 | N(C$_6$H$_5$)$_2$ | — |
| 19 | 4-F—C$_6$H$_4$ | 4-F—C$_6$H$_4$— | 2 | N(CH$_3$)(C$_6$H$_5$) | — |
| 20 | 4-F—C$_6$H$_4$ | 4-F—C$_6$H$_4$— | 2 | N(CH$_3$)$_2$ | — |
| 21 | 4-F—C$_6$H$_4$ | 4-F—C$_6$H$_4$— | 3 | N(C$_6$H$_5$)$_2$ | HCl.0.5H$_2$O |
| 22 | 4-F—C$_6$H$_4$ | 4-F—C$_6$H$_4$— | 3 | N(CH$_3$)$_2$ | 1.5 oxalate |
| 23 | 4-F—C$_6$H$_4$ | 4-F—C$_6$H$_4$— | 3 | NHC$_6$H$_5$ | oxalate.0.5IPA |
| 24 | 4-F—C$_6$H$_4$ | 4-F—C$_6$H$_4$— | 3 | N(CH$_3$)C$_6$H$_6$ | HCl.0.5H$_2$O |

-continued

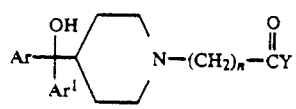

| Ex | Ar | Ar¹ | n | Y | Salt |
|---|---|---|---|---|---|
| 25 | 4-F—$C_6H_4$ | 4-F—$C_6H_4$— | 3 | $NH_2$ | — |
| 26 | 4-F—$C_6H_4$ | 4-F—$C_6H_4$— | 3 | $NH_2$ | oxalate |
| 27 | 4-F—$C_6H_4$ | 4-F—$C_6H_4$— | 1 | $NHCH_3$ | — |
| 28 | 4-F—$C_6H_4$ | 4-F—$C_6H_4$— | 4 | $NHCH_3$ | — |
| 29 | 4-F—$C_6H_4$ | 4-F—$C_6H_4$— | 5 | $N(CH_3)_2$ | oxalate |
| 30 | 4-F—$C_6H_4$ | 4-F—$C_6H_4$— | 1 | OH | $0.5H_2O$ |
| 31a | $C_6H_5$— | $C_6H_5$— | 3 | $NHCH_3$ | — |
| 31b | 4-$CH_3C_6H_4$— | 4-$CH_3C_6H_4$— | 3 | $NHCH_3$ | — |
| 31c | 4-$CH_3OC_6H_4$— | 4-$CH_3OC_6H_4$— | 3 | $NHCH_3$ | — |
| 31d | 4-Cl—$C_6H_4$ | 4-$ClC_6H_4$— | 3 | $NHCH_3$ | — |
| 31e | 4-$FC_6H_4$— | $C_6H_5$— | 3 | $NHCH_3$ | — |
| 31f | 3,4-$diFC_6H_3$— | 3,4-$diFC_6H_4$— | 3 | $NHCH_3$ | — |
| 31g | 3-$FC_6H_4$— | 3-$FC_6H_4$— | 3 | $NHCH_3$ | — |
| 31h | 4-$FC_6H_4$— | 2-pyridinyl | 3 | $NHCH_3$ | — |
| 32a | $C_6H_5$— | $C_6H_5$— | 2 | $NHCH_3$ | — |
| 32b | 4-$CH_3C_6H_4$— | 4-$CH_3C_6H_4$— | 2 | $NHCH_3$ | — |
| 32c | 4-$CH_3OC_6H_4$— | 4-$CH_3OC_6H_4$— | 2 | $NHCH_3$ | — |
| 32d | 4-$ClC_6H_4$— | 4-$ClC_6H_4$— | 2 | $NHCH_3$ | — |
| 32e | 4-$FC_6H_4$— | $C_6H_4$— | 2 | $NHCH_3$ | — |
| 32f | 3,4-$diFC_6H_3$— | 3,4-$diFC_6H_3$— | 2 | $NHCH_3$ | — |
| 32g | 3-$FC_6H_4$— | 3-$FC_6H_4$— | 2 | $NHCH_3$ | — |
| 32h | 4-$FC_6H_4$— | 2-pyridinyl | 2 | $NHCH_3$ | — |
| 33a | $C_6H_5$— | $C_6H_5$— | 4 | $N(CH_3)_2$ | — |
| 33b | 4-$CH_3C_6H_4$— | 4-$CH_3C_6H_4$— | 4 | $N(CH_3)_2$ | — |
| 33c | 4-$CH_3OC_6H_4$— | 4-$CH_3OC_6H_4$— | 4 | $N(CH_3)_2$ | — |
| 33d | 4-$ClC_6H_4$— | 4-$ClC_6H_4$— | 4 | $N(CH_3)_2$ | — |
| 33e | 4-$FC_6H_4$— | $C_6H_5$— | 4 | $N(CH_3)_2$ | — |
| 33f | 3,4-$diFC_6H_3$— | 3,4-$diFC_6H_3$— | 4 | $N(CH_3)_2$ | — |
| 33g | 3-$FC_6H_4$— | 3-$FC_6H_4$— | 4 | $N(CH_3)_2$ | — |
| 33h | 4-$FC_6H_4$— | 2-pyridinyl | 4 | $N(CH_3)_2$ | — |
| 34a | $C_6H_5$— | $C_6H_5$— | 5 | $OC_2H_5$ | — |
| 34b | 4-$CH_3C_6H_4$— | 4-$CH_3C_6H_4$— | 5 | $OC_2H_5$ | — |
| 34c | 4-$CH_3OC_6H_4$— | 4-$CH_3OC_6H_4$— | 5 | $OC_2H_5$ | — |
| 34d | 4-$ClC_6H_4$— | 4-$ClC_6H_4$— | 5 | $OC_2H_5$ | — |
| 34e | 4-$FC_6H_4$— | $C_6H_5$— | 5 | $OC_2H_5$ | — |
| 34f | 3,4-$diFC_6H_3$— | 3,4-$diFC_6H_3$— | 5 | $OC_2H_5$ | — |
| 34g | 3-$FC_6H_4$— | 3-$FC_6H_4$— | 5 | $OC_2H_5$ | — |
| 34h | 4-$FC_6H_4$— | 2-pyridinyl | 5 | $OC_2H_5$ | — |
| 35a | $C_6H_5$— | $C_6H_5$— | 8 | $OC_2H_5$ | — |
| 35b | 4-$CH_3C_6H_4$— | 4-$CH_3C_6H_4$— | 8 | $OC_2H_5$ | — |
| 35c | 4-$CH_3OC_6H_4$— | 4-$CH_3OC_6H_4$— | 8 | $OC_2H_5$ | — |
| 35d | 4-$ClC_6H_4$— | 4-$ClC_6H_4$— | 8 | $OC_2H_5$ | — |
| 35e | 4-$FC_6H_4$— | $C_6H_5$— | 8 | $OC_2H_5$ | — |
| 35f | 3,4-$diFC_6H_3$— | 3,4-$diFC_6H_3$— | 8 | $OC_2H_5$ | — |
| 35g | 3-$FC_6H_4$— | 3-$FC_6H_4$— | 8 | $OC_2H_5$ | — |
| 35h | 4-$FC_6H_4$— | 2-pyridinyl | 8 | $OC_2H_5$ | — |
| 36a | $C_6H_5$— | $C_6H_5$— | 3 | $N(CH_3)_2$ | — |
| 36b | 4-$CH_3C_6H_4$— | 4-$CH_3C_6H_4$— | 3 | $N(CH_3)_2$ | — |
| 36c | 4-$CH_3OC_6H_4$— | 4-$CH_3OC_6H_4$— | 3 | $N(CH_3)_2$ | — |
| 36d | 4-$ClC_6H_4$— | 4-$ClC_6H_4$— | 3 | $N(CH_3)_2$ | — |
| 36e | 4-$FC_6H_4$— | $C_6H_5$— | 3 | $N(CH_3)_2$ | — |
| 36f | 3,4-$diFC_6H_3$— | 3,4-$diFC_6H_3$— | 3 | $N(CH_3)_2$ | — |
| 36g | 3-$FC_6H_4$— | 3-$FC_6H_4$— | 3 | $N(CH_3)_2$ | — |
| 36h | 4-$FC_6H_4$— | 2-pyridinyl | 3 | $N(CH_3)_2$ | — |
| 37a | $C_6H_5$— | $C_6H_5$— | 4 | $NHCH_3$ | — |
| 37b | 4-$CH_3C_6H_4$— | 4-$CH_3C_6H_4$— | 4 | $NHCH_3$ | — |
| 37c | 4-$CH_3OC_6H_4$— | 4-$CH_3OC_6H_4$— | 4 | $NHCH_3$ | — |
| 37d | 4-$ClC_6H_4$— | 4-$ClC_6H_4$— | 4 | $NHCH_3$ | — |
| 37e | 4-$FC_6H_4$— | $C_6H_5$— | 4 | $NHCH_3$ | — |
| 37f | 3,4-$diFC_6H_3$— | 3,4-$diFC_6H_3$— | 4 | $NHCH_3$ | — |
| 37g | 3-$FC_6H_4$— | 3-$FC_6H_4$— | 4 | $NHCH_3$ | — |
| 37h | 4-$FC_6H_4$— | 2-pyridinyl | 4 | $NHCH_3$ | — |
| 38a | $C_6H_5$— | $C_6H_5$— | 5 | $N(CH_3)_2$ | — |
| 38b | 4-$CH_3C_6H_4$— | 4-$CH_3C_6H_4$— | 5 | $N(CH_3)_2$ | — |
| 38c | 4-$CH_3OC_6H_4$— | 4-$CH_3OC_6H_4$— | 5 | $N(CH_3)_2$ | — |
| 38d | 4-$ClC_6H_4$— | 4-$ClC_6H_4$— | 5 | $N(CH_3)_2$ | — |
| 38e | 4-$FC_6H_4$— | $C_6H_5$— | 5 | $N(CH_3)_2$ | — |
| 38f | 3,4-$diFC_6H_3$— | 3,4-$diFC_6H_3$— | 5 | $N(CH_3)_2$ | — |
| 38g | 3-$FC_6H_4$— | 3-$FC_6H_4$— | 5 | $N(CH_3)_2$ | — |
| 38h | 4-$FC_6H_4$— | 2-pyridinyl | 5 | $N(CH_3)_2$ | — |

PHARMACOLOGY METHODS

Antiallergy Screening Method—Rats

As stated above, the primary screening method used to demonstrate antiallergy properties of the compounds of Formula I is a modification of the procedure of R. R. Martel and J. Klicius, International Archives Allergy Appl. Immunology, Vol. 54, pp 205–209 (1977) which measures the effect of oral administration of the compounds on the volume of a rat paw which was previously injected with anti-egg albumin serum following egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scrambler. Random number tables are used to determine the groups receiving the control, reference and test articles. On the test day, the right foot volume of each rat is determined plethysmographically using the hairline as the reference point. Volume of this foot is measured with a mercury filled tube that is connected to a P23A Statham ® pressure transducer that in turn is connected to a linear Cole Parmer ® recorder (Model No. 225). The instrument is adjusted so that a pen deflection of 50 mm is equivalent to 1 ml volume. Separately, the reference and test compounds and control articles are dissolved or suspended in 0.5% Tween 80 in distilled water. Sonification is used to facilitate dissolution or reduce particle size. The animals are dosed orally (10 ml/kg) at 1 hr prior to the intravenous injection of the antigen, 2 mg of egg albumin in 0.2 ml of sterile saline. Thirty minutes later the right foot volume is measured again and edema is determined by difference. Results are expressed as the average foot edema (ml)±S.D. A significant decrease ($p < 0.05$) in edema of the treated group from that of the control group is considered as indicative of antiallergic activity. The results are acceptable only if the group receiving the reference article shows a significant decrease in foot edema. The foot volume for each animal is measured twice, once prior to dosing and again 30 min following the intravenous administration of antigen. Data is analyzed with the Dunnett's t-test that compares several treated groups with a control group. Differences between groups are determined by the studentized Range Test. Regression analysis may be used to determine relative potency. Table 2 below shows data obtained for representative novel compounds of this invention.

TABLE II

Antiallergy Screening Test. Passive Foot Anaphylaxis

| Example No. | % Reduction in Paw Volume | |
|---|---|---|
| | Test[1] | Reference[2] |
| 1 | −31 | −67 |
| 2 | −60 | −73 |
| 3 | −98 | −64 |
| 10 | −34 | −74 |
| 20 | −92 | −87 |
| 22 | −98 | −75 |
| 28 | −75 | −58 |
| 29 | −89 | −58 |

[1]test drug 10 mg/kg/PO
[2]theophylline 100 mg/kg, PO

Pharmaceutical Compositions and Administration

Compositions for administration to living animals are comprised of at least one of the compounds of Formula I according to the antiallergy method of the invention in association with a pharmaceutical carrier or excipient. Effective quantities of the compounds may be administered in any one of various ways, for example, orally as in elixirs, capsules, tablets or coated tablets, parenterally in the form of sterile solutions, suspensions, and in some cases intravenously in the form of sterile solutions, intranasally and to the throat or bronchial region in the form of drops, sprays, aerosols and powders, etc. or cutaneously as topical ointments, solutions, powders, etc. Suitable tableting excipients include lactose, potato and maize starches, talc, gelatin, stearic and silica acids, magnesium stearate and polyvinyl pyrrolidone.

For parenteral administration, the carrier or excipient can be comprised of a sterile parenterally acceptable liquid; e.g., water or arachis oil contained in ampoules.

Advantageously, the compositions are formulated as dosage units, each unit being adapted to supply a fixed dose of active ingredients. Tablets, coated tablets, capsules, ampoules, sprays and suppositories are examples of preferred dosage forms. It is only necessary that the active inredient constitute an effective amount such that a suitable effecive dosage will be consistent with the dosage form employed, in multiples if necessary. The exact individual dosages, as well as daily dosages, will of course be determined according to standard medical principles under the direction of a physician or veterinarian. Generally, the pharmacology tests on guinea pigs in comparison to certain other anti-allergy drugs suggest an effective dose for an adult will be in the range of 0.5 to 10 mg for the more active compounds with a daily dosage amounting to about 2 to 40 mg/day.

Based on the animal data, unit dosages containing an amount of compound equivalent to about 0.01 to 0.1 mg of active drug per kilogram of body weight are contemplated. Daily dosages to about 0.05 to 0.5 mg/kg of body weight are contemplated for humans and obviously several small dosage forms may be administered at one time. However, the amount of the active compounds administered need not be limited by these contemplations due to uncertainty in transposing animal data to human treatment.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

I claim:

1. A compound of the formula:

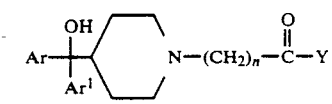

wherein Ar and $Ar^1$, same or different, are pyridinyl or

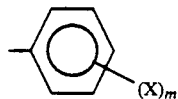

where X is selected from H, CF$_3$, halogen, loweralkyl, loweralkoxy, or hydroxy and m is 1-3;

n is 1-12;

Y is —OH, —O$^\ominus$M$^\oplus$, O-loweralkyl or —O—aryl;

M$^\oplus$ is a pharmaceutically acceptable metal ion; or a pharmaceutically acceptable salt thereof.

2. A compound of claim 1 wherein the compound is 4-bis(4-fluorophenyl)hydroxymethyl)-1-piperidineacetic acid ethyl ester or a pharmaceutically acceptable salt thereof.

3. A compound of claim 1 wherein the compound is 4-(bis(4-fluorophenyl)hydroxymethyl)-1-piperidinepropanoic acid ethyl ester or a pharmaceutically acceptable salt thereof.

4. A compound of claim 1 wherein the compound is 4-(bis(4-fluorophenyl)hydroxymethyl)-1-piperidinebutanoic acid ethyl ester or a pharmaceutically acceptable salt thereof.

5. A compound of claim 1 wherein the compound is 4-(bis(4-fluorophenyl)hydroxymethyl)-1-piperidinepentanoic acid ethyl ester or a pharmaceutically acceptable salt thereof.

6. A compound of claim 1 wherein the compound is 4-(bis(4-fluorophenyl)hydroxymethyl)-1-piperidineheptanoic acid ethyl ester or a pharmaceutically acceptable salt thereof.

7. A compound of claim 1 wherein the compound is 4-(bis(4-fluorophenyl)hydroxymethyl)-1-piperidinehexanoic acid ethyl ester or a pharmaceutically acceptable salt thereof.

8. A compound of claim 1 wherein the compound is 4-(bis(4-fluorophenyl)hydroxymethyl)-1-piperidineoctanoic acid ethyl ester or a pharmaceutically acceptable salt thereof.

9. A compound of claim 1 wherein the compound is 4-(bis(4-fluorophenyl)hydroxymethyl)-1-piperidinedecanoic acid ethyl ester or a pharmaceutically acceptable salt thereof.

10. A compound of claim 1 wherein the compound is 4-(bis(4-fluorophenyl)hydroxymethyl)-1-piperidinenonanoic acid ethyl ester or a pharmaceutically acceptable salt thereof.

11. A compound of claim 1 wherein the compound is 4-(bis(4-fluorophenyl)hydroxymethyl)-1-piperidinebutanoic acid or a pharmaceutically acceptable salt thereof.

12. A compound of claim 1 wherein the compound is 4-(bis(4-fluorophenyl)hydroxymethyl)-1-piperidinepentanoic acid or a pharmaceutically acceptable salt thereof.

13. A compound of claim 1 wherein the compound is 4-(bis(4-fluorophenyl)hydromethyl)-1-piperidineacetic acid or a pharmaceutically acceptable salt thereof.

14. A method of treating a warm blooded animal for allergic disorders which comprises the administration to said animal of an effective amount for treating allergic disorders of a compound having the formula:

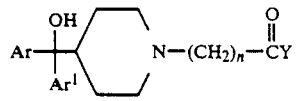

wherein Ar and Ar$^1$, same or different, are pyridinyl or

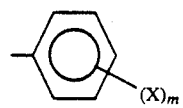

where X is selected from H, CF$_3$, halogen, loweralkyl, loweralkoxy, or hydroxy and m is 1-3;

n is 1-12;

Y is —OH, —O$^\ominus$M$^\oplus$, O-loweralkyl, —O—aryl, or NR$^1$R$^2$ where R$^1$ and R$^2$, same or different, are H, loweralkyl, or aryl;

M$^\oplus$ is a pharmaceutically acceptable metal ion; or a pharmaceutically acceptable salt thereof.

15. A pharmaceutical composition for treating allergic disorders in a warm blooded animal comprised of:

a. an effective amount for treating allergic disorders of a compound having the formula:

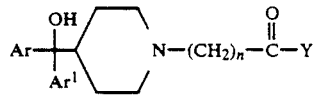

wherein Ar and AR$^1$, same or different are pyridinyl or

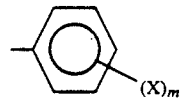

where X is selected from H, CF$_3$, halogen, loweralkyl, loweralkoxy, or hydroxy and m is 1-3;

n is 1-12;

Y is —OH, —O$^\ominus$M$^\ominus$, O-loweralkyl or —O—aryl;

M$^\oplus$ is a pharmaceutically acceptable metal ion; or a pharmaceutically acceptable salt thereof, and b. a pharmaceutically acceptable carrier.

* * * * *